United States Patent [19]
Jackowski

[11] Patent Number: 5,744,358
[45] Date of Patent: *Apr. 28, 1998

[54] METHOD AND DEVICE FOR DIAGNOSING AND DISTINGUISHING CHEST PAIN IN EARLY ONSET THEREOF

[75] Inventor: George Jackowski, Inglewood, Canada

[73] Assignee: Spectral Diagnostics Inc., Toronto, Canada

[*] Notice: The term of this patent shall not extend beyond the expiration date of Pat. Nos. 5,290,678 and 5,604,105.

[21] Appl. No.: 707,594

[22] Filed: Sep. 5, 1996

Related U.S. Application Data

[63] Continuation of Ser. No. 420,298, Apr. 11, 1995, Pat. No. 5,604,105, which is a continuation-in-part of Ser. No. 26,453, Mar. 3, 1993, abandoned, which is a continuation-in-part of Ser. No. 695,381, May 3, 1991, Pat. No. 5,290,678.

[30] Foreign Application Priority Data

Oct. 12, 1990 [CA] Canada .................................. 2027434

[51] Int. Cl.$^6$ ...................... G01N 33/573; G01N 33/558
[52] U.S. Cl. .................. 435/7.4; 422/56; 422/58; 422/60; 422/61; 435/7.94; 435/970; 435/973; 435/975; 436/514; 436/528; 436/530; 436/531; 436/161; 436/164; 436/807; 436/808; 436/810; 436/811
[58] Field of Search ................... 422/55, 56, 58, 422/60, 61; 435/7.9, 7.92, 7.94, 7.4, 969, 970, 973, 975; 436/514, 528, 530, 531, 161, 164, 807, 808, 810, 811

[56] References Cited

U.S. PATENT DOCUMENTS

| | | |
|---|---|---|
| 4,857,453 | 8/1989 | Ullman et al. . |
| 4,900,662 | 2/1990 | Shah et al. . |
| 5,290,678 | 3/1994 | Jackowski . |
| 5,604,105 | 2/1997 | Jackowski .................. 435/7.4 |

FOREIGN PATENT DOCUMENTS

| | | |
|---|---|---|
| 384130 | 8/1990 | European Pat. Off. . |
| WO 91/01498 | 2/1991 | WIPO . |

OTHER PUBLICATIONS

Liew et al. (1994) Proc. Natl. Acad. Sci. USA 91:10645–9.
The Genesis Report 2(2):1–5 (1992).
Jackowski et al. (1989) Circula. Suppl. 80:355 (Abst. #1416).
Katus et al. (1989) J. Mol. Cell Cardiol. 21:1349–53.
Seguin et al. (1989) J. Thorac. Cardiovasc. Surg. 98:397–401.
Wang et al. (1989) Clin. Chimica Acta 181:325–36.
Seguin et al. (1988) J. Thorac. Cardiovasc. Surg. 95:294–7.
Cummins et al. (1987) Am. Heart J. 113:1333–44.
Hoberg et al. (1987) Eur. Heart J. 8:989–94.
Lee et al. (1987) Arch. Intern. Med. 147:115–21.
Lee et al. (1986) Ann. Intern. Med. 105:221–33.
Katus et al. (1984) Am. J. Cardiology 54:964–70.
Baadsgaard et al. (1984) Scand. J. Clin. Lab. Invest. 44:679–82.
"Chossing effective laboratory tests" (1983) Chapter 10, W.B. Sanders Co., Phila., pp. 155–163.
Reese et al. (1981) CMA J. 124:1585–8.
Cummins et al. (1981) Clin. Sci. 60:251–9.

Primary Examiner—Susan Wolski
Attorney, Agent, or Firm—Klauber & Jackson

[57] ABSTRACT

A diagnostic test, and a device for conducting the test, for assessing whether patient chest pain is cardiac in origin and for differentiating between unstable angina and myocardial infarction as a cause of patient chest pain is described. The diagnostic test comprises simultaneously detecting at least three selected cardiac markers with the use of at least three different monoclonal or polyclonal antibody pairs, each member of which is complementary to a different marker, which is released by heart muscle at varying stages after the onset of chest pain and is indicative of the cause of the chest pain.

13 Claims, 10 Drawing Sheets

CK, CK-MB

MYOGLOBIN

MLC

TROPONIN I

TROPONIN T

MHC

TROPOMYOSIN

FIG. 10
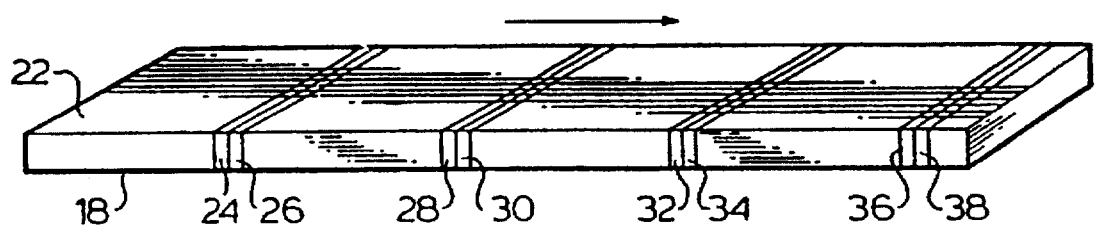
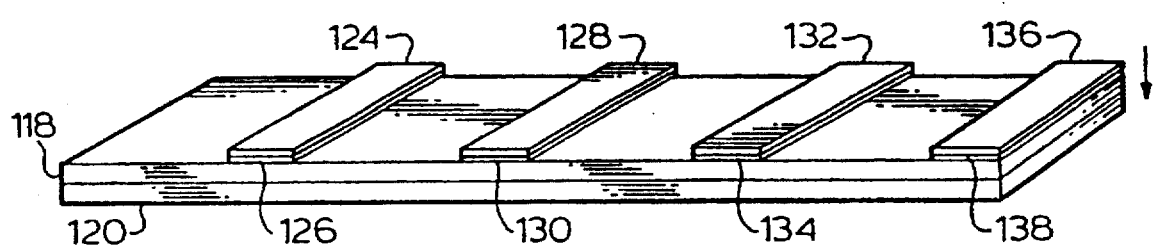
FIG. 11

METHOD AND DEVICE FOR DIAGNOSING AND DISTINGUISHING CHEST PAIN IN EARLY ONSET THEREOF

RELATED APPLICATIONS

This application is a Continuation of application Ser. No. 08/420,298, filed Apr. 11, 1995, now U.S. Pat. No. 5,604, 105, which is in turn, a Continuation-In-Part of application Ser. No. 08/026,453 filed Mar. 3, 1993, now abandoned, which is in turn, a Continuation-In-Part of application Ser. No. 07/695,381, filed May 3, 1991, now U.S. Pat. No. 5,290,678, issued Mar. 1, 1994, all by the inventor herein. Priority is hereby claimed in accordance with 35 U.S.C. 120. The present application further claims priority to Canadian Application Serial No. 2,027,434, filed Oct. 12, 1990, under 35 U.S.C. 119.

FIELD OF INVENTION

This invention relates to a diagnostic tests and devices for conducting such tests at the point of care or in a diagnostic laboratory for accurate, simple, and rapid assessment of chest pain. In particular, the invention relates to differential diagnosis of the origin of chest pain, e.g., whether the pain is cardiac in origin, and for differentiating between unstable angina ("UA"), myocardial infarction ("MI"), congestive heart failure ("CHF"), and other ischemic events affecting the heart, at early onset of patient chest pain. The invention further relates to diagnosis of the stage of the MI in a patient suffering from MI, and to prognosis of such a patient.

BACKGROUND OF THE INVENTION

In order to fully comprehend the novelty and utility of this invention, it is necessary to appreciate certain concepts and definitions.

The emergency room physician is faced with a dilemma when a patient presents with chest pain. He must determine as soon as possible the cause of the chest pain so that the optimum method of treatment can be selected. Ideally, the physician should know the time that has elapsed from the start of the pain to the time of presentation. Specifically, the physician must know if the pain is cardiac in origin or if it originates from some other source.

Chest pain can result from many causes: gastric discomfort (e.g., indigestion), pulmonary distress, pulmonary embolism, dyspnea, musculoskeletal pain (pulled muscles, bruises) indigestion, pneumothorax, cardiac non-coronary conditions, and acute ischemic coronary syndromes (AICS). Cardiac non-coronary conditions include CHF, syncope, arrhythmias, or pericardial diseases. AICS include myocardial infarction, unstable angina, and stable angina.

Ischemic Event

The term "ischemic event" as used herein refers to UA and to MI. This invention permits the emergency room physician to determine within a short period of time, i.e., within one-half hour, if the patient is presenting with an ischemic event or for some other reason. Moreover, it will permit the physician to determine if the ischemic event is UA or MI and, if it is MI, whether the event started less than six hours or more than six hours before presentation.

Cardiac Markers

It has been known for many years that during a cardiac event, heart tissue releases certain molecules, typically protein molecules which are characteristic of the event. Certain of them are released as a result of both UA and MI, others are released as a result of MI. It has been suggested that these markers, often called analytes, be employed in antigen/antibody reactions to recognize the cause of a cardiac event. Efforts along these lines have been generally unsuccessful for a variety of reasons, principally the time required for clinical recognition of the marker and its concentration or level in the blood coupled with the lack of sensitivity and specificity of the tests which have been devised.

Sensitivity and Specificity

"Sensitivity" as used herein refers to the ability of an antibody to recognize and react with its analyte antigen when the analyte is present at very low concentration in a mixture, i.e., blood, serum, plasma or other blood preparation when that mixture contains relatively large numbers of other components. Sensitivity in antigen/antibody reactions is achieved principally by using antibodies with high affinity for their antigens.

"Specificity" as used herein refers (a) to the specificity of an antibody for an analyte, i.e., there is no, or minimal, cross reaction of the antibody with other materials in the sample under test; and (b) to the specificity of the source of the antibody, i.e., did it originate in heart tissue or some other tissue and therefore facilitate diagnosis.

These different types of specificity will be referred to herein as "ischemic specificity," i.e., the antibodies recognize ischemic markers and "diagnostic or tissue specificity," i.e., the antibodies originate from a specific tissue and therefore permit a correct and prompt diagnosis. In other words, they are tissue specific. If they originate only from heart tissue, they are cardiac specific.

Many ischemic markers are known to which antibodies, either monoclonal or polyclonal, have been produced or can be produced by procedures well known to the skilled artisan. A large number of these markers are released as a result of both UA and MI. Others are released only as a result of MI. Many of them are not tissue specific. They originate not only in heart tissue but also in muscle or other body tissue. Their tissue specificity is not cardiac specificity. Some of them are specific for MI and are also cardiac specific. These markers are especially useful in this invention because they have high diagnostic specificity.

The Problem

At first blush, it would appear that the physician could recognize UA and MI simply by selecting cardiac markers or analytes with appropriate ischemic sensitivity and diagnostic sensitivity and identifying them with antibodies having the required antigen/antibody reactivity.

There are several problems which complicate such a simple solution. One is that many cardiac markers are normally present in blood at low levels. It is necessary therefore to identify the markers when they are present at elevated levels. Another is that the increase in concentration of cardiac markers above level with the passage of time is not a straight line curve. Several markers increase to maximum concentration in a relatively short period. The concentration then drops off only to rise again after another period of time. Others do not appear initially, but only after several hours.

It is apparent then that time is a critical factor in the diagnostic procedure. The criticality of time is even more important since it is known that the type of treatment administered may be lifesaving if employed in one time period and life threatening if employed in another.

Angina and Myocardial Infarction

Stable angina results from a sudden contraction of the smaller arteries which supply blood to the heart muscle. The contraction of these blood vessels, the coronary arteries and their branches, results in hypoxia and reduction of nutrients reaching the heart. Individuals perceive this condition as pain and a number of other symptoms. Typically, there is pain in the chest in the region of the heart, pain in the left shoulder and pain in the inner side of the left arm. This pain can be accompanied with breathlessness, apprehension, and sweating. The symptoms are usually associated with exertion such as from exercise, or emotional stress, and will abate with rest. However, even a typical group of symptoms as given above, is not conclusive evidence that the heart is involved. There are a number of conditions which simulate angina, for example mental anxiety.

UA is a form of angina in which the pain attacks become increasingly frequent, and the pain is initiated with less provocation. The pain has a crescendo pattern, increasing gradually to a climax. In contrast to stable angina, UA can occur while the patient is at rest. Frequently, UA derives from the development of atherosclerotic plaques or like obstructive and generally insoluble matter in the arterial vasculature.

Approximately 12 to 18 percent of patients with UA will proceed to an MI. A sudden insufficiency of the arterial blood supply to the heart due to thrombi, emboli, vascular torsion, or pressure, usually caused by a clot lodged in a coronary artery, produces a region of dead or dying tissue (necrosis) in the muscle of the heart.

Diagnosis of the cause of chest pain requires differentiation between these conditions, which is difficult because of the similarity of the symptoms. Nevertheless, an accurate diagnosis is critical to the health of a patient suffering from chest pain, particularly if the cause is MI. If less than six hours have elapsed from the time of the onset of a myocardial infarction, then thrombolytic therapy is available and effective to minimize or even reverse the loss of heart tissue. After six hours, the effectiveness of thrombolytic therapy diminishes rapidly. Thrombolytic therapy based on a misdiagnosis of chest pain that is not caused by MI carries with it the risks attendant to the compromise of the patient's clot forming ability, and, for example, might lead to cerebral hemorrhage. In the extreme situation thrombolytic therapy may actually cause a myocardial infarction which can result in death. This is possible, inasmuch as the nature of the clot or blockage resulting from MI differs from that of UA. In the latter instance, the clot origin is frequently the result of the buildup of calcium or other like deposits that are insoluble, and whose treatment by a thrombolytic agent may cause an attack on the adjacent arterial wall thus dislodging the plaque and permitting it to travel through the vasculature and thereby possibly form an insoluble blockage.

If the physician can quickly recognize that the chest pain is not an ischemic event, other therapies are available. These therapies range from the administration of acetylsalicylic acid and the administration of vasodilators (such as nitroglycerin), to treatment with blood thinning drugs. Although the treatment of angina, particularly UA, is not as urgent as the treatment of MI, prompt effective treatment can avert more serious complications, as well as greatly increase patient comfort. On the other hand, mis-diagnosis of chest pain has a serious economic consequence. Cardiac care is expensive, and the admission of patients who do not need it wastes medical resources.

Notwithstanding the economic disadvantage of admitting patients for cardiac care unnecessarily, physicians must balance the potentially severe consequences of an inappropriate discharge. The balance of saving a life versus unnecessary expense dictates a conservative approach. Thus, physicians tend to admit patients if the diagnosis is uncertain. As a result, as few as 30% of patients admitted to some coronary care units outside the United States are ultimately diagnosed as having MI. Yet even with this conservative approach, about 4% of patients with acute MI are incorrectly perceived as being at low risk and are sent home from the emergency room, usually with severe consequences that are often both medical and legal in nature (Lee et al. *Arch. Intern. Med.* 147, 115–121, 1987). These statistics vary somewhat from country to country, but in the United States are still compelling, in that greater than 60% of the patients are admitted, while only 30% of these actually require treatment.

In the past, emergency diagnosis of MI depended on physician acuity in evaluating various criteria, including family history, the patient's medical history (e.g., hypertension, hyperlipidemia or hypercholesterolemia), and an assessment of a patient's symptoms, such as chest pain or pressure, possibly radiating down the arm and up the neck, fatigue, sense of impending doom, shortness of breath, pallor, cold clammy skin, peripheral cyanosis, or rapid thready pulse. Although these symptoms are suggestive of an ischemic event, clinical decisions are usually based on the patient's history and a single electrocardiogram (ECG). While patients whose ECG tests are negative generally do well, the diagnostic specificity of the ECG is only 51% in the initial phases of chest pain. ECG cannot provide a conclusive diagnosis until after the heart has suffered severe damage. Therefore, ECG is not suitable for early detection of MI.

In normal heart tissue, the cell membrane is intact and in juxtaposition to the blood vessels allowing nutrients and oxygen to pass through, and the contractile proteins are well-organized. Myoglobin and other cardiac markers may be present in the blood at normal levels. In a condition of UA, interrupted blood flow causes the heart to undergo ischemic changes. The cell membrane becomes damaged permitting the passage of certain cardiac proteins from the heart into the blood stream. During MI, and in the first six hours after the onset thereof, a lack of blood flow causes the heart cells to begin to die. During this myocardia necrosis, the membrane becomes even more disrupted enabling the passage of small molecules into the blood stream. During MI, but after the first six hours from the onset of chest pain, the myofibrils become extremely disorganized. At this time larger protein molecules which may serve as markers pass through the membrane.

Several enzymatic cardiac tests have been used together with ECG to confirm MI. These tests employ markers such as serum glutamic oxalacetic transaminase/aspartate transferase (SGOT/AST), lactate dehydrogenase (LDH), creatine kinase (CK), or CK-MB (a myocardial isoform of CK). However, there is no single enzymatic cardiac test which enables the emergency department physician to identify the source of chest pain as cardiac or non-cardiac, or more importantly, to distinguish MI from UA. For example, Lee et al. (*Arch. Intern. Med.* 147, 115–121, 1987), in their evaluation of CK and CK-MB for diagnosing MI, found that single values of cardiac enzymes are not sensitive enough to be used to exclude MI. In their study, 43% of patients with myocardial infarction when tested more than 12 hours after the onset of pain had normal total CK levels.

SGOT/AST is found in high concentration in heart muscle. Serum tests to determine levels of SGOT have been used in diagnosing myocardial infarction. However, SGOT only begins to rise about 8–10 hours following the onset of chest pain, peaks within 24–36 hours and returns to normal after 5–7 days. Thus, SGOT is not particularly helpful in diagnosing myocardial infarction in an emergency setting at an early stage of patient chest pain. Also, SGOT is not specific to cardiac muscle. It is found in many tissues, including skeletal muscle, liver, and kidney, and can be released as a result of intra muscular injections, shock, during liver disease, and hepatic congestion. This marker is of little value in detecting specific cardiac tissue injury at a time early enough be relevant for the most effective treatment, and without excluding a host of other potential indications.

LDH is an enzyme found in high concentration in many tissues, including heart, skeletal muscle, and liver. Enzymatic tests to detect the presence of LDH in serum have been used to diagnose MI. There are five common isotypes of this protein: the heart contains predominantly LDH1 and LDH2. LDH levels begin to rise 24–36 hours after the onset of chest pain, and peak after 48–72 hours, returning to normal after 4–8 days. LDH is therefore not useful as an indicia of MI at an early stage of patient chest pain. In addition, LDH is not specific to cardiac damage and appears with pulmonary embolism, hemolysis, hepatic congestion, renal disease, and skeletal muscle damage.

CK is an enzyme found in muscle tissue. CK catalyses the conversion of creatine and adenosine triphosphate (ATP) to phosphocreatine and adenosine diphosphate (ADP). One of several CK isoenzymes is CK-MB, found primarily but not exclusively in cardiac tissue. CK-MB is a sensitive marker for the detection of myocardial infarction, as it is released from damaged myocardium tissue. CK-MB thereafter is present in the serum of an affected individual. CK-MM which derives from striated and cardiac muscle is the subject of an immunoassay (mass concentration) that has recently been proposed as a diagnostic test for myocardial infarction. A method describing the use of CK-MM is disclosed in U.S. Pat. No. 4,900,662 to Shah, entitled "CK-MM Myocardial Infarction Immunoassay". Shah discloses a method for determining the initial elevated concentration level of CK-MM-a, an isoform of CK-MM, and CK-MM-a formed by carboxypeptidase cleavage of lysine from CK-MM, and CK-MM-b, concurrently in patient serum following a myocardial infarction. FIG. 1 illustrates the concentration of CK in the serum of a patient as a function of time (Lee et al. *Ann. Intern. Med.* 105, 221–233, 1986).

However, there are difficulties with the use of CK-MB alone as a diagnostic marker. First, serum levels of CK-MB are not elevated until 6–8 hours after the onset of myocardial infarction, and do not peak until after 12 hours, making early emergency diagnosis and treatment difficult. Second, the enzymatic test for CK-MB must be conducted in a laboratory by trained laboratory technicians. In non-urban locations, it may not be feasible to conduct the assay for CK enzymatic activity and interpret the results expeditiously, resulting in delay in diagnosis, increasing the cost in human terms (if necessary thrombolytic treatment is delayed) or economic terms (by mis-utilization of a cardiac care bed). Third, the presence of CK-MB in normal skeletal muscle tissue renders tests for this isoenzyme less cardiac specific, and the diagnosis less certain. Previous studies report falsely elevated levels of CK and CK-MB in patients without acute ischemic heart disease, but rather as a result of muscle injury. This has important implications for monitoring cardiac ischemic conditions secondary to some other procedures or injuries. For example, monitoring CK-MB in a post-operative patient would not be useful as a diagnostic test for myocardial infarction as CK-MB levels would already be elevated from the surgery. Furthermore, as noted previously (Lee et al. *Arch. Intern. Med.* 147, 115–121, 1987), many patients with myocardial infarction show normal levels of CK-MB.

Other biochemical markers which have been used in the prior art to test for myocardial infarction include cystolic enzymes. More recently, such markers have been considered and include the muscle oxygen transporting protein myoglobin, muscle structural proteins, i.e. proteins that constitute and/or maintain the structural integrity of the cells, and contractile proteins such as myofibrillar proteins. Structural proteins may also be found in sub-cellular organelles such as the mitochondria, lysosomes, and the sarcolemma, and include cytosolic proteins, lysosomal proteins, sarcoplasmic proteins, sarcoplasmic reticulum proteins, golgi apparatus proteins, nuclear proteins, nucleolar proteins, and mitochondrial proteins. Particular cardiac structural proteins include the following: Actin, $\alpha$-Actin, vascular, $\beta$-Actin, Actin-binding protein, Actin-related protein, Centrosome-associated actin homologue, $\alpha$-Actinin, Skeletal muscle $\alpha$2 actinin, Assembly protein AP50, Cofilin, Cytokeratin, Desmin, Dynein-associated polypeptide, Filamin, Hemopoietic proteoglycan core protein, Microfibril-associated glycoprotein, Microtubule-associated protein, Microtubule-assembled protein, Mitotic kinesin-like protein, Nestin, Non-erythroid band-e like protein, Skelemin, Tensin, Epithelial tropomyosin, $\alpha$-Tubulin, $\beta$-Tubulin, and Vimentin.

Contractile proteins are those associated with and participating in muscle movement, and include myofibrillar proteins such as myosin light chain (MLC), myosin heavy chain (MHC), troponin (Tn), and tropomyosin. Particular proteins are set forth in the following nonlimiting list: $\alpha$-Actin, $\alpha$-Cardiac actin, $\alpha$-Cardiac myosin heavy chain, $\beta$-Myosin heavy chain, Myosin alkali light chain, Myosin light chain, Myosin light chain 1V/Sb isoform, Myosin regulatory light chain, 20-kDa myosin light chain, Ventricular myosin light chain 1, Ventricular myosin light chain 2, Tropomyosin, Cardiac troponin C, Cardiac troponin I and Cardiac troponin T.

Immunoassays have been used to test for the presence of these cardiac markers. Unfortunately, tests for these markers can be inconclusive. One such test is based on myoglobin. Myoglobin is a protein located in muscle cell cytoplasm near the cell membrane. This proximity to the membrane results in its expulsion from the cell as soon as the membrane becomes abnormally permeable, e.g., during an ischemic event. Myoglobin is detectable in the serum within 1.5 hours of the onset of cardiac related chest pain caused by MI. In such instances, myoglobin and CK-MB levels are elevated. FIG. 2 illustrates the concentration of myoglobin in the serum as a function of time during the first ten hours after onset of chest pain due to an ischemic event (Grenadier E. et al. *Am. Heart J.* 105, 408–416, 1981; Seguin J. et al. *J. Thorac. Cardiovasc. Surg.* 95, 294–297, 1988).

However, the level of myoglobin by itself is not a useful marker. Myoglobin is not tissue specific and can also be present during such diverse conditions as shock, renal disease, rhabdomyolysis, and myopathies. Additionally, myoglobin concentrations in serum and plasma generally depend on age and sex and vary over a wide range in normal healthy humans. Serum concentrations up to 90 µg/l are generally regarded as the upper limit of the reference range for healthy people. Therefore, what may be a normal level for one individual may be indicative of a serious problem in another individual, making diagnosis appreciably less accurate than would be desirable. For example, Reese et al. (*CMA Journal*, 124, 1585–1588, 1981) found that 2 out of 5 of his control healthy young men who were engaged in a vigorous game of floor hockey in the evening previous to the test showed high serum myoglobin levels. Thus, strenuous activity, which is a consideration in evaluating the cause of chest pain, can provide a false-positive test result. Additionally, myoglobin concentration peaks in six hours or less and then drops off to an apparent minimum during the next few hours. Since it may not be possible to precisely fix the duration of the pain, the physician is unable to determine if thrombolytic therapy may be lifesaving or life threatening.

MLCs are highly sensitive ischemic markers for UA and MI. MLCs appear in the serum rapidly, and their levels remain elevated for up to 10 days following myocardial necrosis. FIG. 3 illustrates the concentration of MLC in patient serum as a function of time (Wang J. et al. *Clin. Chimica. Acta* 181, 325–336, 1989; Jackowski G. et al. *Circulation Suppl.* 11, 355, 1989). MLC also has prognostic value in determining the success of thrombolytic therapy. Higher levels of MLC indicate a worse prognosis and also correspond to a larger infarction. Falling levels over several days indicate a tendency towards patient recovery, whereas spiking or staccato patterns indicate a tendency towards infarction and a need for intervention.

There are two principal types of MLC known as MLC1 and MLC2, which exist as a soluble pool in the myocardial cell cytoplasm and also integral with the myosin myofibril. In the ventricular muscle, MLC2, and perhaps MLC1, is identical with the isotype expressed in slow skeletal muscle. MLC1 is elevated in 80–85% of the patients with cardiac pain. Thus, MLC1 is a very sensitive ischemic marker and is quite tissue specific.

Low molecular weight cardiac proteins (LMWCP) have been used as cardiac markers. Examples of such cardiac markers include components of the contractile apparatus, namely, troponin, including troponin-T, troponin-I, and troponin-C; mitochondrial enzymes, such as triose P isomerase; low molecular weight polypeptides which are readily released from the heart; and sarcolemmal membrane proteins or protein fragments which may be released early after the onset of ischemia, in particular, a 15 kd sarcolemma protein and a 100 kd complex glycoprotein that are cardiac specific. However, to date diagnostic tests and methods that make use of these markers have not been developed. They may be employed in the practice of this invention because they are ischemic markers which are cardiac specific.

The cardiac isotype troponin-I inhibits the interaction between actin and myosin molecules during rest periods between contractions of the heart muscle. Troponin-I appears in serum of patient within 4–6 hours after MI and remains elevated for 7–8 days. FIG. 4 illustrates the concentration of troponin-I as a function of time (Cummins B. et al. *Am. Heart J.* 113, 1333–1344, 1987). Troponin-I is a cardiac specific ischemic marker which is especially useful in the practice of this invention.

Troponin-T is part of the troponin-tropomyosin complex of the thin filament, that is part of the muscle contractile apparatus, and that contains actin and tropomyosin regulatory elements. Troponin-T serves as a link between the tropolyosin backbone and the troponin-I/troponin-C complex. Troponin-T is a basic protein and has isotypes in cardiac and fast and slow skeletal muscles. It appears in serum within 3 hours of the onset of chest pain and remains elevated for at least 10 days following MI. FIG. 5 illustrates the concentration of troponin-T as a function of time (Katus H. A. et al. *J. Mol. Cell Cardiol.* 21, 1349–1353, 1989). Troponin-T follows a biphasic release pattern. It is very specific for MI, despite being present in other tissues. Despite its lack of tissue specificity, it is useful in this invention because of its rapid appearance.

Myosin heavy chains (MHC), and tropomyosin, are heavy molecular weight proteins which are useful as cardiac markers. MHC is part of the major contractile protein of muscle. Fragments of MHC can be released from the ventricle into serum after myocardial cell necrosis and subsequent irreversible membrane injury MI. MHC fragments do not appear quickly in the serum. MHCs remain elevated for at least 10 days following MI and peak levels of MHC are observed 4 days after MI. FIG. 6 illustrates the concentration of MHC as a function of time (Leger J. O. C. et al. *Eur. J. of Clin. Invet.* 15, 422–429, 1985; Seguin J. R. et al. *J Thorac. Cardiovasc. Surg.* 98, 397–401, 1989). The area under the MHC release curve correlates very well with the extent of myocardial cell damage. However, MHC levels are of little clinical value during the acute phase of MI as they are released at the four-day mark, although their measurement is important in determining the extent of post-MI damage.

Tropomyosin is a dimer formed from two polypeptide which are part of the regulatory system in muscle contraction. Tropomyosin is detectable in serum approximately 7–8 hours after MI. FIG. 7 illustrates the concentration of tropomyosin as a function of time (Cummins P. et al. *Clin. Sci.* 60, 251–259, 1981). However, tropomyosin is not cardiac specific since it is elevated in conditions of skeletal muscle trauma.

From all of the above, it is apparent that specific tests and correspondingly individual markers have been identified and considered for use in the detection of ischemic events; however, without sufficient predictability to be considered successful.

Thus far, no tests have been developed apart from that set forth in U.S. Pat. No. 5,290,678, that have favorably addressed even a part of this problem.

A further aspect of the diagnosis of cardiac disorders derives from the temporal variability with which patents present themselves and are examined. It is never certain as to when a particular patient suffering chest pain may enlist medical examination, and one must be able to examine and rapidly diagnose patients who may have experienced the onset of chest pain for from minutes to hours. This is significant as each of the analytes that have been measured in the past exhibits a time-dependent variation in its appearance, presence and concentration, so that the examination of a patient at a different point along the time continuum might possibly yield a different diagnosis if the particular marker in question were the only factor under measurement.

Accordingly, a further specific objective of an effective of a cardiac test is to achieve a biochemical diagnosis within a short period of time, suitably within one-half hour from the time that the patient presents. To this extent, and in keeping with the temporal variability of patient conditions, the term "simultaneous" as it may apply to the performance of such a cardiac test and the retrieval of the results, for purposes of a diagnosis, is intended to refer to the ability to achieve such chemical diagnosis of chest pain within such shortened period, and therefore includes the measurement of the multiple analytes or markers in accordance with the present invention whether performed within a single device having capabilities for such conjoint detection and measurement, or by means of the use of individual such devices, each capable of detecting and indicating the presence and amount of a particular marker or analyte, provided that such detection and measurement are carried out within a period of time in which the detection and measurement of one analyte is meaningful with respect to the other analytes detected and measured.

As noted above, there is an urgent need in the art to accurately and rapidly diagnose the cause of chest pain, so as to distinguish cardiac causes from non-cardiac causes. There is a further acute need to diagnose the cardiac disorder causing chest pain if it is caused by the heart, to distinguish acute ischemic coronary syndromes from other cardiac disorders, and most particularly, to distinguish UA from MI. Although many markers for ischemic events have been identified, none of these markers are competent individually for a conclusive diagnosis. Some of the markers appear too late to be of any help in treating incipient MI, or treating UA to avert MI. Others are not cardiac specific; release of these markers from other muscle tissue or organs such as the liver as a result of vigorous exercise, surgery, disease, and the like, any one of which may be, and frequently are, associated with chest pain, may lead to an incorrect diagnosis or, more disturbingly, to incorrect mis-diagnosis. The economic and social impact of mis-diagnosis is staggering. Nevertheless, diagnostic tests with the required speed, accuracy and versatility are not available, and it is therefore toward the development of such a test that the present invention is directed.

SUMMARY OF THE INVENTION

In accordance with the present invention, a method and corresponding materials and devices are disclosed for the rapid, accurate and sensitive diagnosis of chest pain in a patient to distinguish an ischemic event from other causes, to distinguish between UA and MI and, if the latter, to determine as closely as possible the time of the event. The method comprises detecting and measuring at least three markers associated with cardiac disorder simultaneously as defined herein. In a particular embodiment of the invention, the markers or analytes are simultaneously detected whereby the presence of said analytes in amounts above normal enables the diagnostician to differentiate between pain of cardiac and non-cardiac origin. Such detection may take place by the disposition of the patient's blood sample on a single device having the ability to detect all three markers, or by the disposition of portions of the sample on separate devices or media capable of detecting individual markers. The important point is that the presence of the selected markers above normal concentrations be detected simultaneously.

An aspect of the invention resides in the detection of the minimum of three markers that together present an array of data that is capable in combination of distinguishing between ischemic and non-ischemic events. Further, should it be concluded that the pain is of cardiac origin, the results of the method will differentiate between the conditions of UA and MI. This ability is attributable in part to the ability of the present method and the corresponding kits and devices embodying the same, to offer results that reflect both high sensitivity and high specificity, as defined herein. The combination of the diverse markers measured hereby, and the extent of the underlying diversity of such markers in both qualitative and temporal terms bears significantly on the quality of the diagnostic results. Moreover, the speed with which the method may be practiced and the results conclusively obtained make it possible to rapidly arrive at a diagnosis and thereby facilitate the early implementation of appropriate therapy such as the administration of thrombolytic agents if the event is within the critical initial period of approximately 6 hours, or angioplasty, bypass surgery or other treatment if the period is more than six hours.

More specifically, the present method comprises:

i. contacting a sample, such as blood, serum or plasma, suspected of having the markers with at least three binding partners, e.g., antibodies, wherein at least one of each binding partner is specific for one of each marker suspected of being present in the sample, under conditions that provide for immunospecific binding of the binding partner to the marker for which it is specific so as to form a binding partner-marker binding pair; and ii. reacting the antibody-marker binding pair with a second capture antibody to form a multiple antibody-marker composite;

iii. detecting the presence of the composite.

As stated above, the method of the invention involves simultaneously assessing the level of each of the said markers present in a biological sample, such as, for example, a sample of blood, serum, plasma, or a preparation thereof, from an individual believed to be suffering from an ischemic event. The markers to be evaluated are all associated with a cardiac disorder; however, each of the three differs from the other in certain defined properties.

The antibodies are selected so that:

i. the first antibody pair is reactive with a selected ischemic marker;

ii. the second antibody pair is characterized by diagnostic specificity for an MI marker which reaches detectable levels above normal either before or after about six hours. This antibody pair does not necessarily have high sensitivity for the target marker;

iii. the third antibody pair reacts with an ischemic marker which is cardiac specific.

In preferred embodiments there will be a fourth antibody pair similar to the second antibody pair but with release kinetics opposite to those of the second pair. If the second pair peaks at less than six hours, the fourth pair should peak at more than six hours and vice versa. In this preferred embodiment, if only the second antibody pair is positive, the other pairs indicate an MI and the fourth pair is negative, the physician will know that the patient has presented within the critical six-hour period and thrombolytic therapy is indicated. If both the second and fourth pair are positive and the other pairs indicate an MI, the physician will know that the patient has not presented within the critical period and other therapeutic treatments are indicated.

Typically useful ischemic markers which are tested for with the first antibody pair, include myosin light chain I, myosin light chain II and tropomyosin.

Myoglobin, LDH and SGOT are representative of markers to be tested for with the second antibody pair. One may also use carbonic anhydrase and fatty acid binding protein as well.

Amongst the useful markers for the third antibody pair are troponin I, troponin T and glycogen phosphorylase BB, and others set forth in Table III.

Typical cardiac markers for the fourth antibody pair are myosin heavy chain and tropomyosin, as well as selected listed in Tables III and IV.

Testing with only three antibody pairs is indicated when it is known that the period between onset of pain and presentation is either more or less than six hours. Testing with four antibody pairs will be indicated when the duration of the relevant period is unknown.

The level of each of the markers is assessed by contacting the sample suspected of having the markers with at least three antibodies, wherein at least one of each of the antibodies is specific for one of each of the markers suspected of being present in the sample, under conditions that provide for immunospecific binding of the antibody specific for the marker (the detector antibody) to the marker for which it is specific so as to form an antibody-marker binding pair; and detecting the level of the antibody-marker binding pair with a second or capture antibody and detecting the presence of the marker at a level above normal by forming a multiple antibody-marker reaction product or composite.

The present invention advantageously provides a sensitive, specific, and rapid diagnostic test to permit prompt selection of a treatment protocol. The tests according to the invention can be performed at the point of care by medically trained personnel. For example, emergency medical service workers can perform a test of the invention at the site of a medical emergency or in the ambulance on the way to the hospital. Similarly, medical personal in the emergency room, cardiac care facility or other point of care location at a hospital can perform a test of the invention themselves. Naturally and where clinically appropriate, the patient sample such as blood, plasma, or serum, may be provided to a hospital laboratory to perform the test. The test results indicate to a medical practitioner, e.g., a physician, whether the chest pain is cardiac in nature or whether the patient is suffering from an ischemic event, and the nature and time of such event. The tests can, of course, be formatted for use with read-out facilities available in an ambulance, in an emergency room, in a doctor's office, or in a cardiac care facility.

In some cases patients may experience anginal pain for several days. Approximately 12 to 18 percent of such patients with unstable angina will proceed to experience MI. The test of the present invention, which can distinguish UA and MI, allows for constant monitoring so that onset of MI in cases such as these, where a patient may have been experiencing chest pain for several days, and therefore the exact time of onset of chest pain becomes irrelevant, is timely detected. Similarly, the tests of the present invention are useful for monitoring individuals in whom chest pain may be ignored, e.g., those who have had a chest injury or surgery. As with an acute myocardial infarction, early intervention is critical to effective treatment of this sort of condition, also referred to as "slow-onset" MI.

The invention extends to test materials including reagents in a kit form for the practice of the inventive method. The materials comprise the binding partners that are specific to the markers under detection, and in one embodiment, comprise the antibody or antibodies, each of which is specific for one of each of the markers, the presence of which is to be determined. In this embodiment, one antibody of each pair specific for a particular marker is irreversibly immobilized onto a solid support; this antibody is alternately referred to hereinafter as a capture antibody. The other antibody specific for the same marker is labeled, and is capable of moving with a sample to the location on the solid support of the capture antibody. This antibody is sometimes referred to herein as the detection antibody.

The present invention correspondingly extends to devices for conducting the assays, i.e., a device for early determination of the cause of chest pain for at early onset thereof. According to one aspect of this embodiment of the invention there is provided a device comprising a housing means containing a membrane unit or section, with a detector section and a capture section, preferably with a filter section. The detector section contains at least three detector antibodies specific to an epitope on each of the cardiac markers to be tested for in a patient's sample of blood, serum or plasma. The capture section contains at least three capture antibodies specific to another epitope of each of the markers to be detected. The capture section is positioned distal to the position of the detector section, wherein the capture antibodies are irreversibly immobilized in the capture section, the detector antibodies are reversibly immobilized in the detector section and migrate with the sample into the capture section, when the device is in use. The detector antibodies may be suitably labeled to give a measurable reaction when the marker is present an is bound in accordance with the process of this invention.

Binding of the binding partner or antibody to its cognate antigen, the marker, in a sample can be detected by other detection means, such as optical detection, biosensors, homogenous immunoassay formats, and the like. Particular optical sensing systems and corresponding devices are contemplated and are discussed in greater detail hereinafter.

Accordingly, it is a principal object of the present invention to provide a method that is rapid, sensitive and economical for the detection of cardiac disorder in patients experiencing chest.

It is a further object of the present invention to provide a method as aforesaid that is capable of accurately differentiating between chest pain of a cardiac and non-cardiac origin with a high degree of sensitivity and specificity.

It is a further object of the invention to provide a fast, accurate, and sensitive assay for the differential diagnosis of either UA or MI in a patient who has cardiac ischemic event.

It is a still further object of the present invention to provide a method that is capable of practice by means of both manual and automated devices.

It is yet a further object of the present invention to provide materials and devices for the detection of cardiac disorders, including such devices as employ optical sensor technology.

Other objects and advantages will become apparent to those skilled in the art from a consideration of the following detailed description taken in conjunction with the following illustrative drawings.

BRIEF DESCRIPTION OF THE DRAWINGS

FIG. 10 is an oblique view of the membrane of the embodiment of FIG. 8;

FIG. 11 is an oblique view of a second embodiment of the membrane;

DETAILED DESCRIPTION OF THE INVENTION

Figure 1:
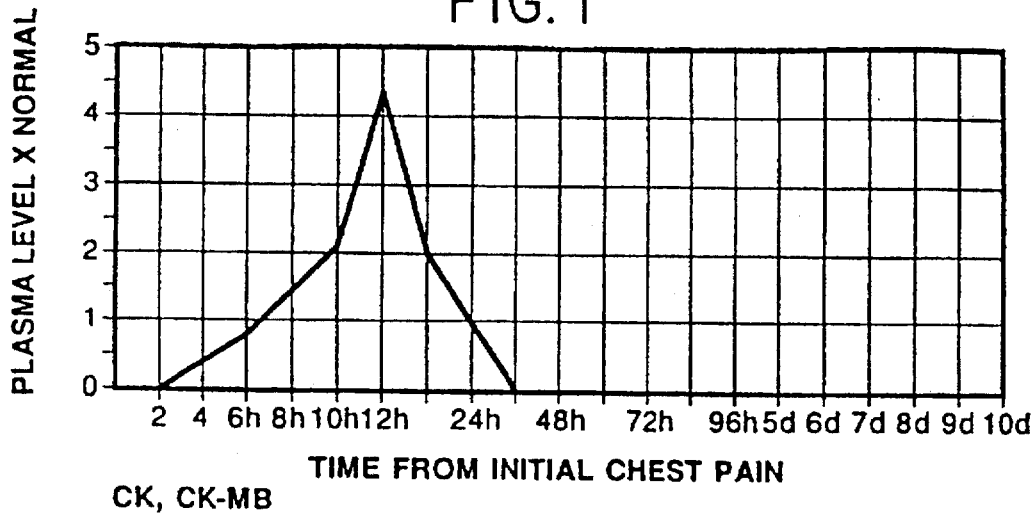
FIG. 1 is a graph illustrating the level of CK in serum as a function of time.
Figure 2:
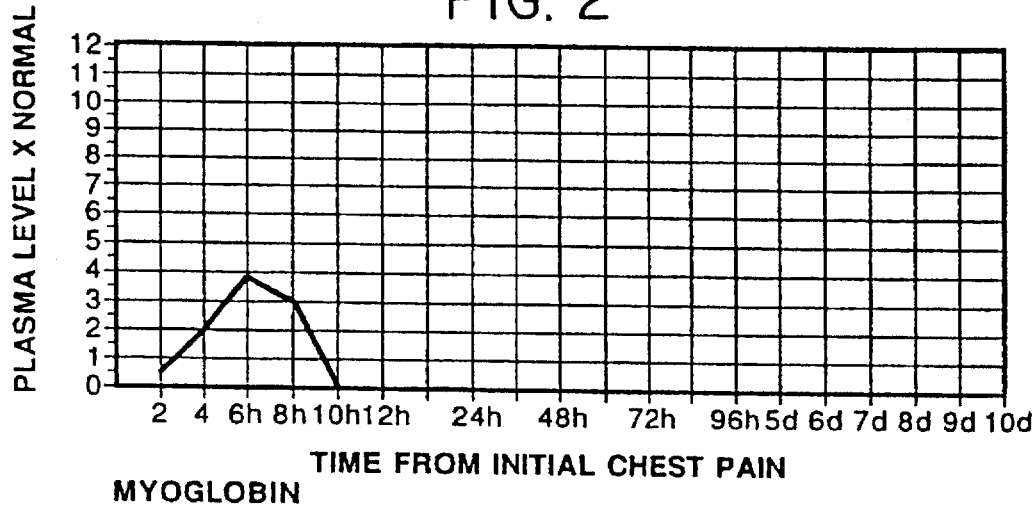
FIG. 2 is a graph illustrating the level of myoglobin in serum as a function of time.
Figure 3:
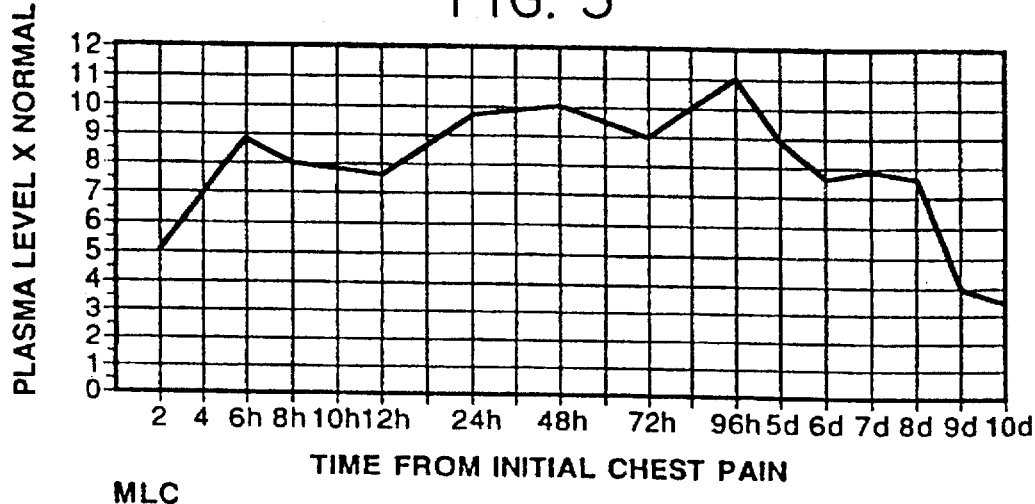
FIG. 3 is a graph illustrating the level of MLC in serum as a function of time.
Figure 4:
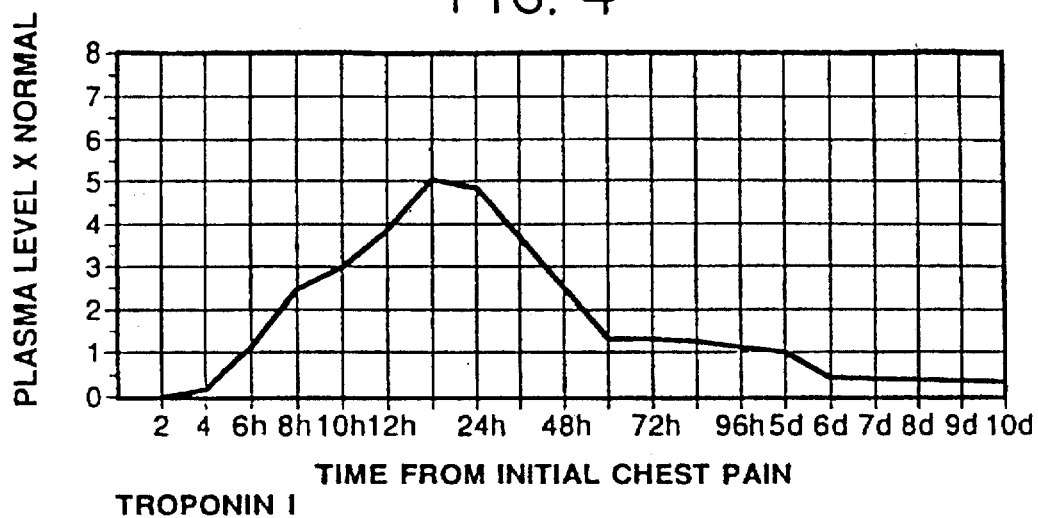
FIG. 4 is a graph illustrating the level of troponin-I in serum as a function of time.
Figure 5:
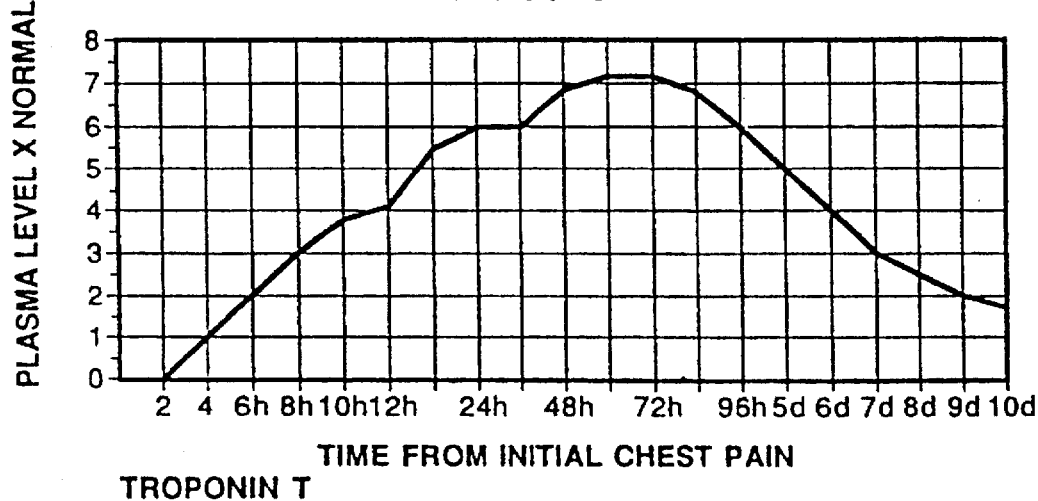
FIG. 5 is a graph illustrating the level of troponin-T in serum as a function of time.
Figure 6:
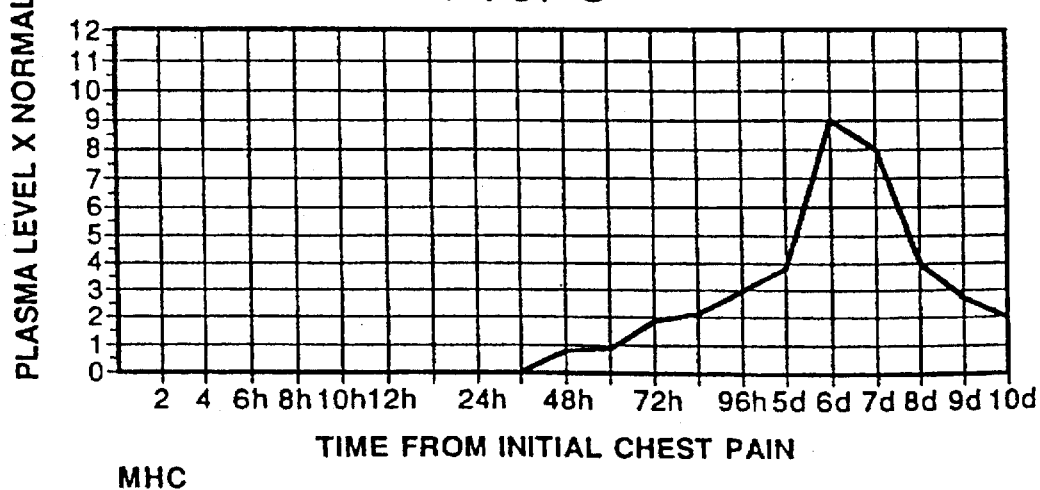
FIG. 6 is a graph illustrating the level of MHC in serum as a function of time.
Figure 7:
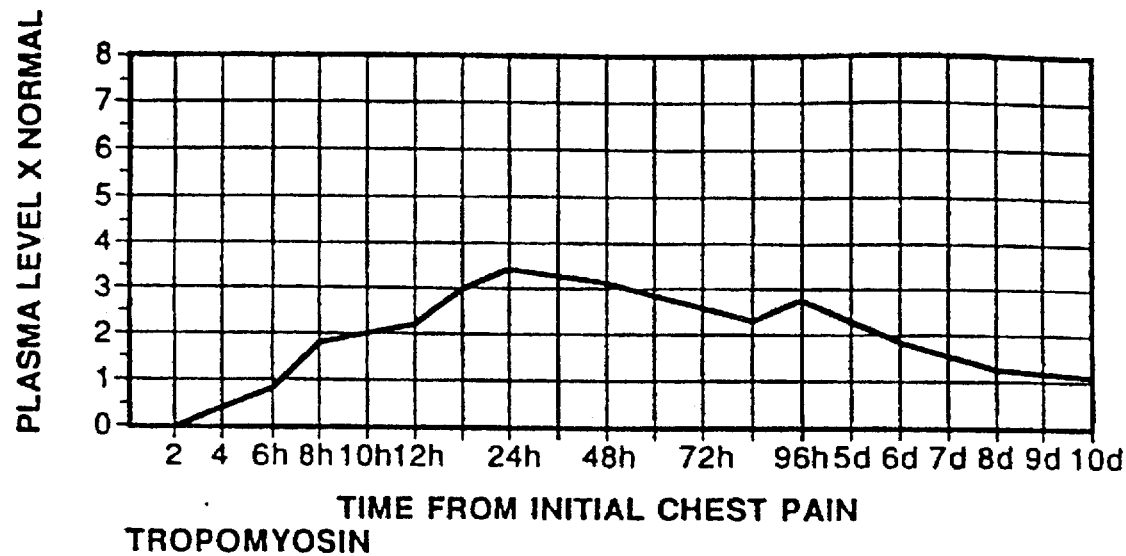
FIG. 7 is a graph illustrating the level of tropomyosin in serum as a function of time.

According to the present invention, there are provided diagnostic tests and corresponding devices for determining if chest pain is cardiac in nature, and for distinguishing between UA and MI. This test and device can also be used to determine the stage of MI if the patient is suffering from the same.

When a patient is experiencing chest pain, protein markers or analytes released from the heart reveal whether or not the pain involves the heart. These proteins also indicate whether the chest pain results from UA or MI. As stated above, the present invention proceeds by the simultaneous detection of the presence of an above normal level of at least three of such markers with selected properties thereby achieving the advantages of specificity, sensitivity and temporal versatility. The cardiac status of these patients may be rapidly and accurately diagnosed without limitation as to the post-onset time of their presentation and examination.

The terms "cardiac disorder", "cardiac event", "cardiac episode" or "cardiac distress" are all used interchangeably herein to refer to diseases or disorders affecting the heart. As discussed above, chest pain can result from many causes: gastric discomfort (e.g., indigestion), pulmonary distress, pulmonary embolism, dyspnea, musculoskeletal pain (pulled muscles, bruises,) indigestion, pneumothorax, cardiac non-coronary conditions, and acute ischemic coronary syndromes (AICS). Cardiac non-coronary conditions include CHF, syncope, arrhythmias, or pericardial diseases. AICS include myocardial infarction, unstable angina, and stable angina.

As used herein, the term "marker" refers to a protein or other molecule that is released from the heart during an ischemic event. Such markers include, but are not limited to, proteins or isoforms of proteins that are unique to the heart muscle, and proteins or isoforms thereof that are found in tissues other than heart muscle.

The markers of the present invention are released into the blood. Thus, the invention contemplates assessing the level of the markers in blood, or any blood product that contains them such as, but not limited to, plasma, serum, cytolyzed blood (e.g., by treatment with hypotonic buffer or detergents; see, e.g., International Patent Publication No. WO 92/08981, published May 29, 1992), and dilutions and preparations thereof.

The term "above normal" or "above threshold" are used herein to refer to a level of a marker that is greater than the level of the marker observed in normal individuals. For some markers, no or infinitesimally low levels of the markers may be present. For other markers, notably myoglobin, detectable levels may be present normally in blood. Thus, the terms further contemplate a level that is significantly above the level found in patients. The term "significantly" refers to statistical significance, and generally means at least a two-fold greater level of the marker is present. However, a significant difference between levels of markers depends on the sensitivity of the assay employed, and must be taken into account for each marker assay.

Markers

The markers which can be used according to the present invention are any cardiac molecules, typically proteins that pass out from the heart cells as the cells become damaged, either during UA or MI as a result of an ischemic event. These proteins can be either in the native form or can be immunologically detectable fragments of the protein, resulting, for example, from photolytic digestion of the protein. When the terms "marker" or "analyte" are used, they are intended to include fragments thereof that can be immunologically detected. By "immunologically detectable" is meant that the protein fragments contain an epitope that is specifically recognized by a cognate antibody.

Proteins which are useful in accordance with the present invention can be primarily classed according to their function, as to whether they are structural or contractile. As defined earlier, structural proteins are so classified herein to the extent that they constitute and/or maintain the structural integrity of the cells. Representative structural proteins including particular protein types are set forth previously and in Table 1, below.

TABLE 1

STRUCTURAL PROTEINS

| | |
|---|---|
| Cytosolic Proteins | Glutamate dehydrogenase |
| | Glutamate pyruvate transaminase |
| | τ-Glutamyl transpeptidase |
| | Aldolase |
| | Isocitrate dehydrogenase |
| | Malate dehydrogenase |
| | Glyceraldehyde phosphate dehydrogenase |
| | Adenylate kinase |
| | Triose-P-Isomerase |
| | CK-MB |
| | CK-MM |
| | CK-BB |
| | Myoglobin |
| | SGOT/AST |
| | LDH-1 |
| | LDH-2 |
| | CK (total) |
| | Acid phosphate |
| | Glycogen Phosphorylase BB |
| | Carbonic Anhydrase II |
| | Acid phosphate |
| | N-Acetyl-β-glucosaminidase |
| | N-Acetyl-β-galactosaminidase |
| | N-Leucyl-β-naphthylamidase |
| | β-Galactosidase |
| | β-Glucuronidase |
| | Fatty Acid Binding Protein |
| | $Ca^{++}$-requiring protease (m-Calpain) |
| | Pyruvate Dehydrogenase |
| | Pyruvate kinase |
| Lysosomal Proteins | Cathepsin D |
| | Cathepsin A |
| | Cathepsin C |
| Sarcoplasmic Proteins | $Ca^{2+}$ ATPase |
| | Phospholamban |
| | Calmodulin |
| | Caldesmon |
| | Adenylate cyclase |
| Sarcoplasmic Reticulum | $Ca^{2+}$ ATPase |
| | Phospholamban |
| | Phospholamban Phosphatase |
| | Annexins |
| | Calsequestrin |
| | $Ca^{2+}$ pumping adenosine triphosphatase |
| | $Ca^{2+}$ transport ATPase |
| | Protein Kinase |
| | Histidine rich calcium binding protein |
| | Protein phosphatase 2A |
| | Protein phosphatase 2C |
| | High affinity calcium binding protein |
| | Low density lipoprotein-binding sarcoplasmic reticulum protein |
| Golgi | Peptide hydrolase |
| | Adenosine diphosphate-ribosylation factor 6 |

TABLE 1-continued

STRUCTURAL PROTEINS

| | |
|---|---|
| | Transferrin |
| | Furin protein |
| | Hexominadase |
| | Soluble proteins |
| | Kinesin |
| | Lysomal glycoprotein |
| | NADH oxidase |
| | Glutamate decarboxylase |
| Nuclear Proteins | Histones, non-histone proteins |
| Nucleolar Proteins | Heterogeneous HRNP non-ribonuclear proteins |
| Mitochondrial Proteins | CK-MB |
| | CK-MB$_2$ |
| | CK-MB$_1$ |
| | CK-MM |
| | CK-MM$_1$ |
| | CK-MM$_3$ |
| | CK-BB |
| | Acontinase |
| | ADP/ATP translocase |
| | Aldolase |
| | Aldolase A |
| | Aldolase A, fibroblast |
| | Aspartate aminotransferase |
| | Carnitine palmitoyltransferase I |
| | Citrate synthase |
| | Creatine kinase M |
| | Cytochrome bc-1 complex core protein |
| | Cytochrome bc-1 complex core protein II |
| | 2,4-Dienoyl-CoA reductase |
| | Dihydrolipoamide dehydrogenase |
| | α-Enolase |
| | Glyceraldehyde-3-phosphate dehydrogenase |
| | Glycogen synthase kinase 3α |
| | Glycogen phosphorylase, brain |
| | H$^+$-ATP synthase subunit b |
| | Inosine-5'-monophosphate dehydrogenase |
| | Ketoacid dehydrogenase kinase |
| | Lactate dehydrogenase A |
| | Lactate dehydrogenase B |
| | Lipoprotein lipase |
| | Malate dehydrogenase |
| | Mitochondrial ATP synthase |
| | Mitochondrial malate dehydrogenase |
| | NADH-cytochrome b5 reductase |
| | NADH-ubiquinone oxidoreductase |
| | Neuroleukin (glucose phosphate isomerase) |
| | Phosphogluconate dehydrogenase |
| | Phosphoglycerate mutase |
| | Phosphofructokinase |
| | Pyruvate kinase M2-type |
| | Transglutaminase |
| | Triose-phosphate isomerase |
| | Ubiquinone oxidoreductase |
| Cytoskeletal | Actin |
| | α-Actinin |
| | Microtubule-associated protein |
| | Epithelial tropomyosin |
| | α-Tubulin |
| | β-Tubulin |
| | Vimentin |
| Extracellular Matrix | Elastin |
| | Extracellular matrix protein BM-40 |
| | Fibronectin, cellular |
| | Fibronectin |
| | Laminin B2 chain |
| | S laminin |
| Membrane-Associated | Amyloid protein |
| | Anion exchange protein 3 |
| | Ca$^{2+}$-ATPase |
| | Cardiac Ca$^{2+}$-release channel (ryanodine receptor) |
| | Chloride channel protein |
| | Cysteine-rich FGF receptor |
| | Fibronectin receptor α subunit |
| | Fibronectin receptor β subunit |
| | Integrin α6 |
| | Interleukin 5 receptor |
| | Junctional sarcoplasmic reticulum glycoprotein |
| | Laminin receptor |
| | Laminin receptor homolog |
| | Lysosomal membrane glycoprotein CD63 |
| | Minimal change nephritis glycoprotein |
| | Na$^+$/Ca$^{2+}$ exchanger |
| | Na$^+$/K$^+$ ATPase |
| | Voltage-dependent anion channel |
| | Voltage-dependent anion channel isoform 1 |
| Miscellaneous Structural | Ca$^{2+}$-dependent protease |
| | Choline kinase |
| | Cyclophilin-like protein |
| | DNA repair helicase |
| | DNA topoisomerase II |
| | Poly(ADP-ribose) polymerase |
| | Sarcolumenin |
| | Ubiquitin |
| | Ubiquitin-activating enzyme E1 |
| Signal Transduction and Cell Regulation | Adenylyl cyclase |
| | Calcium-dependent protein kinase I |
| | cAMP-dependent protein kinase |
| | CAP protein |
| | G$_s$ αsubunit |
| | G$_s$ GTP-binding protein |
| | p190-GAP-associated protein |
| | GTPase |
| | Guanylate cyclase |
| | NAD-ADP ribosyltransferase |
| | Nuclear protein |
| | Nucleic acid-binding protein |
| | 80-kDa protein kinase C substrate |
| | Protein phosphatase 2A catalytic subunit β |
| | Protein-tyrosine phosphatase HPTPβ |
| | A-raf-1 oncogene |
| | RecA-like protein |
| | Rho-GAP protein |
| | Serine-threonine protein kinase |
| | c-syn protooncogene |
| | TSE1 protein kinase A regulatory subunit |
| Transcription and Translation | Chaperonin-like protein |
| | DNA-binding protein |
| | DNA-binding protein A |
| | Elongation factor 1α |
| | Elongation factor 1γ |
| | Elongation factor 2 |
| | Ro ribonucleoprotein autoantigen |
| | HnRNP type A/B protein |
| | Heat shock protein (neurospora) |
| | Heat shock protein HSP70 |
| | HnRNP core protein A1 |
| | Novel hnRNP protein |
| | Initiation factor 4AI |
| | Initiation factor 4B |
| | Poly(a)-binding protein |
| | Acidic ribosomal phosphoprotein |
| | Acidic ribosomal phosphoprotein PO (nonenxact) |
| | Ribosomal protein L3 |
| | Ribosomal protein L4 |
| | Ribosomal protein L5 |
| | Ribosomal protein L6 |
| | Ribosomal protein L7 |
| | Ribosomal protein L8 |
| | Ribosomal protein L18 |
| | Ribosomal protein L19 |
| | Ribosomal protein L29 |
| | Ribosomal protein S3 |
| | Ribosomal protein S4 |
| | Ribosomal protein S6 |
| | Ribosomal protein S9 |
| | Ribosomal protein S19 |
| | Ribosomal protein S20 |
| | Transcription factor ISGF-3 |
| | Zinc finger protein |

Contractile proteins are those participating in muscle movement or action, and include myofibrillar proteins such as those representatively set forth in Table 2, below.

TABLE 2

CONTRACTILE PROTEINS

| Myofibrillar Proteins | Troponin-T |
|---|---|
| | Troponin-I |
| | Troponin-C |
| | Myosin Light Chair |
| | MLC-1 |
| | MLC-2 |
| | Actin |
| | Tropomyosin |
| | α-Actin |
| | α-Cardiac actin |
| | α-Cardiac myosin heavy chain |
| | β-Myosin heavy chain |
| | Myosin light chain IV/SB isoform |
| | Myosin regulatory light chain |
| | 20-kDa myosin light chain |
| | Tropomyosin |

This classification scheme relates to the information available from detection of such proteins. For example, release of small cytosolic proteins is expected to occur rapidly, and may result from unstable angina. Release of myofibrillar proteins, i.e., contractile proteins, is expected to occur later and as a result of severe ischemia or necrosis. Proteins contained in organelles are expected to be released last, since release of these proteins requires disruption of both the cell membrane and the organelle membrane.

Examples of ischemic markers and their time of appearance in cardiac events are listed below in Table 3.

TABLE 3

Ischemic Markers (UA/MI)

| Marker | Time of Presentation | Cardiac Specificity |
|---|---|---|
| Troponin-T | 6 hr> | + |
| Troponin-I | 6 hr> | + |
| MLC-1 | <6 hr | − |
| MLC-2 | <6 hr | − |
| Glycogen Phosphorylase BB | <6 hr | + |
| $Ca^{2+}$ ATPase | <6 hr | − |
| Phospholamban | <6 hr | + |
| Myosin Heavy Chain | 6 hr> | − |
| Actin | <6 hr | − |
| Tropomyosin | 6 hr> | − |
| Calmodulin | <6 hr | − |
| Caldesmon | <6 hr | + |
| Phospholamban phosphatase | <6 hr | + |
| Calsequestrin | <6 hrs | + |
| $Ca^{++}$ pumping adenosine triphosphatase | <6 hrs | + |
| $Ca^{++}$ transport ATPase | <6 hrs | + |
| Adenylate cyclase | <6 hrs | − |
| Protein kinase | <6 hrs | − |
| Histidine rich calcium binding protein | <6 hrs | − |
| Protein phosphatase 2A | <6 hrs | − |
| Protein phosphatase 2C | <6 hrs | − |
| High affinity calcium binding protein | <6 hrs | + |
| Low density lipoprotein-binding sarcoplasmic reticulum protein | 6 hrs> | − |
| $Ca^{++}$-requiring protease (m-calpain) | <6 hrs | + |
| Pyruvate dehydrogenase | <6 hrs | − |

In order to determine the stage of a patient suffering from myocardial infarction, one must be able to differentiate between the various proteins groups which will be found in the blood stream in the early stages of MI, for example, within the first 6 hours after the onset of chest pain, and in later stages of MI, for example after the first 6 hours from the onset of chest pain. Representative markers having the required properties are set forth in Table 4, below.

TABLE 4

MI Specific Markers

| Marker | Time of Presentation |
|---|---|
| Triose-P-Isomerase | 6 hr> |
| CK-MB | 6 hr> |
| CK-MM | 6 hr> |
| CK-BB | 6 hr> |
| Myoglobin | <6 hr |
| SGOT/AST | 6 hr> |
| LDH-1 | 6 hr> |
| LDH-2 | 6 hr> |
| CK total | 6 hr> |
| Carbonic Anhydrase II | 6 hr> |
| Fatty Acid Binding Protein | <6 hr |
| Cathepsin D | 6 hr> |
| CK-MB isoform | 6 hr> |
| $CK-MB_2$ | |
| CK-MM isoform | 6 hr> |
| $CK-MM_1$ | |
| CK-MB isoform | 6 hr> |
| $CK-MB_1$ | |
| CK-MM isoform | 6 hr> |
| $CK-MM_3$ | |
| Cathepsin A | 6 hr> |
| Cathepsin C | 6 hr> |
| Glutamate osaloacetate transaminase | 6 hr> |
| Aldolase | 6 hr> |
| Malate dehydrogenase | 6 hr> |
| β-Glucuronidase | 6 hr> |
| Glyceraldehyde phosphate dehydrogenase | 6 hr> |
| L-Leucyl β-Naphthylamidase | |
| Adenylate kinase | 6 hr> |
| Isocitrate dehydrogenase | 6 hr> |
| Gamma glutamyl transpeptidase | 6 hr> |
| Pyruvate kinase | <6 hr |
| N-Acetyl β-glucosaminidase | 6 hr> |
| N-Acetyl β-galactosamindase | 6 hr> |
| Acid phosphate | <6 hr |
| β-Galactosidase | 6 hr> |

As noted from Table 4, examples of markers which are MI specific and are present in the blood stream within the first 6 hours after the onset of chest pain include myoglobin and fatty acid binding protein. As further noted from Table 4, examples of markers which are MI specific and are present in the blood stream after the first 6 hours subsequent to the onset of chest pain include: triose-p-isomerase, CK-MB, CK-MM, CK-BB, SGOT/AST, LDH-1, LDH-2, CK (total), carbonic anhydrase II and cathepsin D, $CK-MB_2$, $CK-MB_1$, $CK-MM_1$, $CK-MM_3$, cathepsin A and low density lipoprotein-binding sarcoplasmic reticulum protein. Those markers which are also cardiac specific are preferred for the practice of this invention.

The present invention is not limited to the proteins specifically listed in Tables 3 and 4, as any proteins released from damaged cardiac tissue can be used according to the precepts of the invention. A person skilled in the art will readily recognize, based on the teachings of the present invention, what other proteins can be used according to the present invention.

Antibodies to the Markers

As used herein, the term antibody includes polyclonal and monoclonal antibodies of any isotype (IgA, IgG, IgE, IgD, IgM), or an antigen-binding portion thereof, including but not limited to F(ab) and Fv fragments, single chain antibodies, chimeric antibodies, humanized antibodies, and a Fab expression library.

In the most preferred practice of this invention, all of the antibodies will be monoclonal. It is preferred that at least one of the antibodies of each pair be monoclonal.

Antibodies useful as detector and capture antibodies in the present invention may be prepared by standard techniques well known in the art. Polyclonal antibodies may be prepared from the serum of animals such as mice, guinea pigs, rabbits, horses, sheep or goats, which have been immunized against the appropriate antigen (analyte). Specific protocols for the production of polyclonal antibodies are well known in the art. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*.

For preparation of monoclonal antibodies directed toward a marker polypeptide, or fragment, analog, or derivative thereof, any technique that provides for the production of antibody molecules by continuous cell lines in culture may be used. These include but are not limited to the hybridoma technique originally developed by Kohler and Milstein (1975, Nature 256:495–497), as well as the trioma technique, the human B-cell hybridoma technique (Kozbor et al., 1983, Immunology Today 4:72), and the EBV-hybridoma technique to produce human monoclonal antibodies (Cole et al., 1985, in *Monoclonal Antibodies and Cancer Therapy*, Alan R. Liss, Inc., pp. 77–96). In an additional embodiment of the invention, monoclonal antibodies can be produced in germ-free animals utilizing recent technology (PCT/US90/02545). According to the invention, human antibodies may be used and can be obtained by using human hybridomas (Cote et al., 1983, Proc. Natl. Acad. Sci. U.S.A. 80:2026–2030) or by transforming human B cells with EBV virus in vitro (Cole et al., 1985, in *Monoclonal Antibodies and Cancer Therapy*, Alan R. Liss, pp. 77–96). In fact, according to the invention, techniques developed for the production of "chimeric antibodies" (Morrison et al., 1984, J. Bacteriol. 159–870; Neuberger et al., 1984, Nature 312:604–608; Takeda et al., 1985, Nature 314:452–454) by splicing the genes from a mouse antibody molecule specific for a cardiac marker together with genes from a human antibody molecule of appropriate biological activity can be used; such antibodies are within the scope of this invention.

According to the invention, techniques described for the production of single chain antibodies (U.S. Pat. No. 4,946, 778) can be adapted to produce marker-specific single chain antibodies. An additional embodiment of the invention utilizes the techniques described for the construction of Fab expression libraries (Huse et al., 1989, Science 246:1275–1281) to allow rapid and easy identification of monoclonal Fab fragments with the desired specificity for a cardiac marker.

In the production of antibodies, screening for the desired antibody can be accomplished by techniques known in the art, e.g., radioimmunoassay, ELISA (enzyme-linked immunosorbent assay), "sandwich" immunoassays, immunoradiometric assays, gel diffusion precipitin reactions, immunodiffusion assays, in situ immunoassays (using colloidal gold, enzyme or radioisotope labels, for example), Western blots, precipitation reactions, agglutination assays (e.g., gel agglutination assays, hemagglutination assays), complement fixation assays, immunofluorescence assays, protein A assays, and immunoelectrophoresis assays, etc.

Monoclonal antibodies useful in the present invention may be prepared by conventional procedures, generally following the methods of Kohler and Milstein (Nature, 256, 495–497, 1975; Eur. J. Immunol. 6, 511–519, 1976). According to this method, tissue culture adapted mouse myeloma cells are fused to antibody producing cells from immunized mice to obtain the hybrid cells that produce large amounts of a single antibody molecule. The antibody-producing cells are then fused with myeloma cells, cell lines originating from various animals such as mice, rats, rabbits, and humans, can be used, using a suitable fusion promoter. Many mouse myeloma cell lines are known and available generally from members of the academic community and various depositories, such as the American Type Culture Collection, Rockville, Md. The myeloma cell line used should preferably be medium-sensitive so that unfused myeloma cells will not survive in a selective medium, while hybrids will survive.

The immortalized cells (hybridoma) must then be screened, e.g., using a method disclosed above, for those which secrete antibody of the correct immunospecificity. In a specific embodiment, the initial screening is generally carried out using an enzyme-linked immunosorbent assay (ELISA). Specifically, the hybridoma culture supernatants are added to microtiter plates which have been previously coated with the antigen. A bound specific antibody from the culture supernatants can be detected using a labelled second antibody, for example, goat antimouse IgG labelled with peroxidase (commercially available). Cultures that are positive against the antigen are then subjected to cloning by the limiting dilution method. Secondary hybridoma cultures are re-screened as described above, and further positive cultures are then examined using the BIAcore™0 system (Pharmacia Biosensor AB, Uppsala, Sweden). This is a biosensor that utilizes the quantum mechanical phenomenon of Surface Plasmon Resonance (SPR) to detect and analyze the interactions of biological molecules. Detailed theoretical background and procedures are described by R. Karlsson et al. (J. Immunol. Methods, 145, 229, 1991).

The cultures are then evaluated as to whether or not the antibody binds the antigen and to determine the kinetic profile of antigen binding. Selected cultures based on these results are subject to further cloning until culture stability and clonality are obtained. Immediately after hybridization, the fusion products will have approximately 80 chromosomes, and as these cells proceed to divide they will randomly lose some of these chromosomes. The cloning process is to select those cells which still have the chromosomes coding for antibody production. The cloning process is repeated until 100% of the sub-population exhibits the production of a specific antibody, which is indicative of the "stability" of the hybridoma. In addition, hybridoma culture wells often have multiple colonies some of which may be non-producers of antibody. The cloning process allows the selection of a positive hybrid which is derived from a single cell.

Either monoclonal or polyclonal antibodies can be used in the diagnostic test of the present invention. The capture antibody or detector antibody need not be a complete antibody. Fragments of antibodies can be used according to the present invention, and the term "antibody", as used in the present invention, encompasses said fragments.

For example, such fragments may be prepared by use of fd phage according to the procedure of Clackson et al. (1991, Nature 352:624–8) so that generated antibody fragments fused to a minor coat protein of the virus become enriched with antigen in a highly specific manner. This use of phage display libraries could create a single antibody which demonstrates specificity toward a multiplicity of the antigens employed as markers in the diagnostic test of the present invention.

The production of polyclonal antibodies found in egg yolk of an immunized chicken (IgY) described by Polson et al. (1980, Immunol. Comm. 9:495–514) is the preferred method for obtaining antibody to be used in the diagnostic test of the invention. The benefits of chicken IgY over mammalian antibody IgGs include lower cost and substantive increase in yield. In a preferred embodiment, polyclonal antibodies to the protein markers utilized in the diagnostic test, for example, but not limited to myoglobin, muscle creatine kinase, troponin I and myosin light chain, are generated using chickens according to the methods of Gassmann et al. (1990, FASEB J. 4:2528–32).

To this end, the purified protein marker is diluted in 0.01M potassium phosphate buffer (pH 7.2) containing 0.1M NaCl to a final volume of 750 μl and emulsified with an equal volume of complete Freund's adjuvant. The suspension is injected in two sites of the pectoral muscle in laying hens. Future booster injections are administered as described 12 or 20 days following the initial injection.

To purify IgY from the individual eggs, the yolk is separated from the white and yolk skin into a graduated cylinder using deionized water. The yolk suspension is then filled to 30 ml with buffer A comprised of 0.01M potassium phosphate buffer (pH 7.2) containing 0.1M NaCl and mixed with 30 ml of a solution of 7% w/v PEG 6000 diluted in buffer A. The sample is then centrifuged at 14,000×g for 10 min at 4° C., the supernatant filtered, and solid PEG is added to a final concentration of 12% w/v. Centrifugation is repeated and the pellet containing IgY is resuspended in 20 ml of buffer A mixed in an equal volume of a 24% w/v PEG solution in buffer A. The sample is pelleted as described and resuspended in 10 ml of buffer A followed by dialysis against the same buffer. Finally the dialyzed mixture is centrifuged and the supernatant further purified on a DEAE-cellulose column.

Antigens are purified by known techniques used in the separation and purification of biological materials, for example, as described in the preceding references relating to CK-MB, myoglobin, MLC and troponin.

Immunoassay Methods

The present invention provides a method and devices for the simultaneous assay of at least three selected markers, selected as described above, to determine if the cause of chest pain is cardiac in nature, and if so, if it is the result of unstable angina or myocardial infarction. As stated earlier, the term "simultaneous" does not mean that the analysis for each marker must be done concurrently, but such analysis must be done within a time frame (e.g., within about one-half hour following sampling) so that the relative level of each marker can be assessed, and this information used to diagnose the cause of chest pain. Moreover, the sample in which the level of each marker is assessed is preferably a single sample, i.e., a sample drawn at a single point in time from a particular patient. In this way, an accurate diagnosis may be reached regardless of whether the markers are measured in a single device or in separate devices, as the level of each marker simultaneously present in the sample will be assessed to yield meaningful data.

According to the present invention the presence of the selected markers is determined using antibodies specific for each of the said markers, and detecting immunospecific binding of each antibody to its respective cognate marker.

Various means known in the art for detecting immunospecific binding of an antibody to an antigen can be used to detect the binding of each antibody to each marker in accordance with the present invention, e.g., as discussed supra in the section relating to Antibodies to the Markers. An early method of detecting interaction between an antigen and an antibody involved in analysis of the complex is by precipitation in gels. A further method of detecting an analyte-detector antibody binding pair includes the use of radioiodinated detector antibodies or a radioiodinated protein which is reactive with IgG, such as Protein A. These early methods are well known to persons skilled in the art, as reviewed in Methods in Enzymology, 70, 166–198, 1980.

Later methods for determining the presence of an analyte in a sample using only one antibody, included competitive binding assays. In this technique the antibody, which most often would be immobilized onto a solid support, would be exposed to a sample suspected of containing the analyte together with a known quantity of labelled analyte. The two analytes, the labelled analyte and the analyte in the sample would then compete for binding sites on the antibody. Either free labelled analyte or bound labelled analyte is determined and from this measurement the amount of competing analyte in the sample is known. A more complete description of this method is disclosed in "Basic Principles of Antigen-Antibody Reaction", Elvin A. Labat, (Methods in Enzymology, 70, 3–70, 1980). In this example the labelled analyte can be labelled with either a radioisotope or an enzyme label.

More current immunoassays utilize a double antibody method for detecting the presence of an analyte. These techniques are also reviewed in the above referenced volume of Methods in Enzymology. Therefore, according to one embodiment of the present invention, the presence of the individual markers are determined using a pair of antibodies for each of the markers to be detected. One of said pairs of antibodies is referred to herein as a "detector antibody" and the other of said pair of antibodies is referred to herein as a "capture antibody". One embodiment of the present invention thus uses the double antibody sandwich method for detecting the cardiac markers (analytes) in a sample of biological fluid. In this method, the analyte is sandwiched between the detector antibody and the capture antibody, the capture antibody being irreversibly immobilized onto a solid support. The detector antibody would contain a detectable label, in order to identify the presence of the antibody-analyte sandwich and thus the presence of the analyte. Common early forms of solid supports include plates, tubes or beads of polystyrene, all of which are well known in the field of radioimmunoassay and enzyme immunoassay. More recently, a number of porous material such as nylon, nitrocellulose, cellulose acetate, glass fibers and other porous polymers have been employed as solid supports.

Thus, in a specific embodiment, the device of the invention comprises means for conducting an immunochromatographic assay ("immunochromatographic assay device"). Such a device comprises a solid phase means for conducting a liquid. As used herein, the term "solid phase means for conducting a liquid" refers to a solid support that allows migration of a liquid therethrough, e.g., via capillary action. A typical product of this nature is a nitrocellulous membrane which may be prepared by methods well-known to those skilled in the art.

Many immunochromatographic assay means and formats are known in the art, and can be used in the practice of the present invention. Immunochromatographic assays using a membrane as a solid support in a dipstick or flow-through device are well established for use in the clinical laboratory and for alternative, i.e., non-laboratory, site testing. The usual presentation for an immunochromatographic assay device is a membrane (cellulosic or non-cellulosic) enclosed in a plastic holder. The plastic holder keeps the membrane in a suitable configuration in order to ensure correct functioning of the entire device. There are many variations of the basic structure of assay devices. For example, Litman et al. (U.S. Pat. Nos. 5,156,952 and 5,030,558) describe an assay method and device for determining the presence of a minimum amount of an analyte in a sample. Ullman et al. (U.S. Pat. Nos. 5,137,808 and 4,857,453) describe a device to house an assay membrane that includes self-contained liquid reagents to aid sample flow. Dafforn et al. (U.S. Pat. No. 4,981,768) describes a device with ports for applying sample and extra liquid. Assay devices are also described by Corti et al. (European Patent Application No. 89118378.2), Greenquist et al. (U.S. Pat. No. 4,806,312) and Berger et al. (U.S. Pat. No. 5,114,673).

Preferably, the immunochromatographic assay means includes a control to indicate that the assay has proceeded correctly. The control can be a specific binding reactant at a spot more distal from the sample application point on the solid phase support than the detection zone that will bind to labelled reagent in the presence or absence of analyte, thus indicating that the mobilizable receptor has migrated a sufficient distance with the liquid sample to give a meaningful result.

Suitable labels for use in immunochromatographic assays include enzymes, fluorophores, chromophores, radioisotopes, dyes, colloidal gold, colloidal carbon, latex particles, and chemiluminescent agents. When a control marker is employed, the same or different labels may be used for the receptor and control marker.

One embodiment of the present invention uses a flow-through type immunoassay device. Valkirs et al. (U.S. Pat. No. 4,632,901) discloses a device comprising antibody, specific to an antigen analyte, bound to a porous membrane or filter to which is added a liquid sample. As the liquid flows through the membrane, target analytes bind to the antibody. The addition of the sample is followed by the addition of a labelled antibody. The visual detection of the labelled antibody provides an indication of the presence of the target analyte in the sample. Another example of a flow-through device is disclosed by Kromer et al. (EP-A 0 229 359), which describes a reagent delivery system comprising a matrix saturated with a reagent or components thereof dispersed in a water soluble polymer for controlling the dissolution rate of the reagent for delivery to a reaction matrix positioned below the matrix.

In migration type assays, the solid phase support, e.g., membrane, is impregnated with the reagents needed to perform the assay. An analyte detection zone is provided in which labelled analyte is bound and the results of the assay are read.

For example, see Tom et al. (U.S. Pat. No. 4,366,241), and Zuk (EP-A 0 143 574). Migration assay devices usually incorporate within them reagents which have been attached to colored labels such as colloidal gold or carbon, thereby permitting visible detection of the assay results without addition of further substances. See for example, Bernstein (U.S. Pat. No. 4,770,853), May et al. (WO 88/08534), and Ching et al. (EP-A 0 299 428). All of these known types of flow-through devices can be used according to the present invention.

Direct labels are one example of labels which can be used according to the present invention. A direct label has been defined as an entity, which in its natural state, is readily visible, either to the naked eye, or with the aid of an optical filter and/or applied stimulation, e.g. U.V. light, to promote fluorescence. Examples of colored labels which can be used according to the present invention, include metallic sol particles, for example, gold sol particles such as those described by Leuvering (U.S. Pat. No. 4,313,734); dye sol particles such as described by Gribnau et al. (U.S. Pat. No. 4,373,932) and May et al. (WO 88/08534); dyed latex such as described by May, supra, Snyder (EP-A 0 280 559 and 0 281 327); or dyes encapsulated in liposomes as described by Campbell et al. (U.S. Pat. No. 4,703,017). Other direct labels include a radionuclide, a fluorescent moiety or a luminescent moiety. In addition to these direct labelling devices, indirect labels comprising enzymes can also be used according to the present invention. Various types of enzyme linked immunoassays are well known in the art, for example, alkaline phosphatase and horseradish peroxidase, lysozyme, glucose-6-phosphate dehydrogenase, lactate dehydrogenase, urease, these and others have been discussed in detail by Eva Engvall in Enzyme Immunoassay ELISA and EMIT in *Methods in Enzymology*, 70. 419–439, 1980 and in U.S. Pat. No. 4,857,453.

In a specific embodiment, the diagnostic device of the present invention comprises a membrane assembly having a detection section proximal to the point of introduction of the sample, and a capture section downstream therefrom. The detector section contains antibodies (detector antibodies), which will react with any cardiac analytes of the present invention that are present in the sample. The detector antibodies are reversibly immobilized onto the membrane and will migrate with the sample, when in use. It is preferred although not essential, that the detector antibodies are labelled, for example, with a radionuclide, an enzyme, a fluorescent moiety, luminescent moiety or a colored label such as those described in the prior art, and discussed above. Specifically, one could employ a reactive label, so that for example, the antibody would appear gold before capture of the antigen, and would change to purple upon capture.

The capture section which, as stated, is downstream from the detector section, comprises capture antibodies, which are irreversibly immobilized onto the solid support, each antibody immobilized at a different position in the capture section. The antibodies and necessary reagents are immobilized onto the solid support using standard art-recognized techniques, as discussed in the flow-through type immunoassay devices discussed previously. In general, the antibodies absorbed onto the solid supports as a result of hydrophobic interactions between non-polar protein substructures and non-polar support matrix material.

One drawback of such immunochromatographic assay devices is the lack of quantitation. Quantitation is required to some degree to determine whether a marker is present at a level above the threshold level. However, immunochromatographic assays can be formatted to be semiquantitative. The term "semiquantitative" refers to the ability to discriminate between a level that is above the threshold, and a level that is not above the threshold.

In another embodiment of the present invention, the diagnostic test uses a blood sample tube which is commonly used to draw blood samples from patients. The inside wall of the tube acts as a carrier for the monoclonal or polyclonal antibodies and required reagents or detection means needed to produce a measurable signal. In this embodiment the capture antibody is immobilized onto the wall of the test tube. After the sample is drawn from the patient, the user simply shakes the sample with the detector antibodies in the tube so that the detector antibody reacts with any cardiac markers the blood.

It may be necessary to use a sample wherein the red blood cells have been removed, suitably with membrane filtration, so that the red blood cells will not interfere with the analysis of the results. Alternately, the chromogen that is used as the indicator may be selected for its ability to give a signal at a different wavelength, so as to distinguish from the color of the red blood cells. If the analyte is present in the blood, it will be sandwiched between the capture antibody and the detector antibody which contains a suitable label for direct detection or reacts with the reagents in an indirect assay. The solid support (the test tube) can then be rinsed free of unbound labelled material. A variety of solid supports can be used according to this method, for example, test tube walls, plastic cups, beads, plastic balls and cylinders including microtiter plates, paper, and glass fibers.

In another embodiment of the present invention, the different cardiac damage markers are analyzed by the placement of portions of the sample within separate tubes or solid support materials, each containing individual detector antibodies. Alternatively, if each of the detector antibodies are labelled differently, then the test can be performed in a single tube.

In addition, the present invention contemplates use of homogeneous immunoassay formats. One example of such a competitive homogeneous method is found in U.S. Pat. No. 3,817,837 by Rubenstein and Ullman, which describes a technique in which ligand and enzyme-bound-ligand compete for antibody binding sites. Since binding of the antibody to the enzyme-bound-ligand alters its enzymatic activity, the concentration of ligand present can be estimated by measuring the rate at which such a mixture converts substrate to product. Thus, in a homogeneous method, the detectable property of the label is inherently different depending on whether bound or unbound. In its bound state, the label will haver greater or lesser signal intensity. Usually, binding of antibody to the labelled ligand causes a decrease in signal intensity, e.g., when the label is an enzyme. Typical products in this category include the EMIT line of enzyme immunoassays from Syva Company and the TDX line of fluorescence polarization immunoassays from Abbott Diagnostics. A particular homogeneous assay could be prepared with the disposition of all of the analytes on beads, in which event the sample would be introduced and the beads thereafter spun down and detected.

Other examples of biological diagnostic devices which can be used according to the present invention, include the devices described by G. Grenner, P. B. Diagnostics Systems, Inc., in U.S. Pat. Nos. 4,906,439 and 4,918,025. The Grenner '439 device comprises a diagnostic test element and a sample application unit comprising a fluid delivery element that is characterized as having a layer with a plurality of grooves for the delivery of the sample to the test element. Grenner '025 relates to a device which includes a sample introducing means such as a membrane adjacent to which is positioned a capillary containing a fixed reagent and a waste liquid reservoir. Release of the fixed reagent from the capillary completes the reaction after the sample is deposited, and excess liquid is retained by the waste reservoir, so that the device is self contained.

While the measurement with a membrane is preferred, it is to be understood that other techniques and corresponding sensor devices may likewise be used in similar fashion to the above. There are currently available several types of automated assay apparatus which can undertake an assay on a number of samples contemporaneously. These automated assay apparatuses include continuous/random access assay apparatus. Examples of such systems include OPUS™ of PB Diagnostic System, Inc. and the IMX™ Analyzer introduced by Abbott Laboratories of North Chicago, Ill. in 1988. In general, a sample of the test fluid is typically provided in a sample cup and all the process steps including pipetting of the sample into the assay test element, incubation and reading of the signal obtained are carried out automatically. The automated assay systems generally include a series of work stations each of which performs one of the steps in the test procedure. The assay element may be transported from one work station to the next by various means such as a carousel or movable rack to enable the test steps to be accomplished sequentially. The assay elements may also include reservoirs for storing reagents, mixing fluids, diluting samples, etc. The assay elements also include an opening to permit administration of a predetermined amount of a sample fluid, and if necessary, any other required reagent to a porous member. The sample element may also include a window to allow a signal obtained as a result of the process steps, typically a fluorescent or a colorimetric change in the reagents present on the porous member to be read, such as by a means of a spectroscopy or fluorometer which are included within the assay system. The automated assay instruments of PB Diagnostic Systems, Inc. are described in U.S. Pat. Nos. 5,051,237; 5,138,868; 5,141,871 and 5,147, 609.

A description of the IMX Analyzer is included in the "Abbott IMX Automated Bench Top Immunochemistry Analyzer System" by Fiore, M. et al, *Clinical Chemistry*, 35, No. 9, 1988. A further example of these analyzers has been described in U.S. Pat. No. 4,956,148 entitled "Locking Rack and Disposable Sample Cartridge" issued to C. J. Grandone on Sep. 1, 1990, and assigned to Abbott Laboratories, which describes a carousel for carrying a plurality of reaction cells for use in connection with the Abbott IMX™ system. A further development in the art has been described in Canadian Patent Application 2,069,531, to Chadwick M. Dunn et al, assigned to Abbott Laboratories, wherein the immunochemistry analyzer system, described in this prior art application, has the capability of testing for up to three or four analytes in a single batch during a single run using currently available instrumentation. The system described in the Canadian application referred to above enables the users to group three small batches of assays together rather than run three separate analysis. These automated analyzers can be used in accordance with the present invention.

A further class of immunochemical analyzer systems which can be used in practicing the present invention, are the biosensors or optical immunosensor systems. In general an optical biosensor is a device which uses optical principles quantitatively to convert chemical or biochemical concentrations or activities of interest into electrical signals. These systems can be grouped into four major categories: reflection techniques; surface plasmon resonance; fiber optic techniques and integrated optic devices. Reflection techniques include ellipsometry, multiple integral reflection spectroscopy, and fluorescent capillary fill devices. Fiber-optic techniques include evanescent field fluorescence, optical fiber capillary tube, and fiber optic fluorescence sensors. Integrated optic devices include planer evanescent field fluorescence, input grading coupler immunosensor, Mach-Zehnder interferometer, Hartman interferometer and difference interferometer sensors. Holographic detection of binding reactions is accomplished detecting the presence of a holographic image that is generated at a predetermined image location when one reactant of a binding pair binds to an immobilized second reactant of the binding pair (see U.S. Pat. No. 5,352,582, issued Oct. 4, 1994 to Lichtenwalter et al.). Examples of optical immunosensors are described in general in a review article by G. A. Robins (Advances in Biosensors), Vol. 1, pp. 229–256, 1991. More specific description of these devices are found for example in U.S. Pat. Nos. 4,810,658; 4,978,503; and 5,186,897; R. A. Brady et al. (Phil. Trans. R. Soc. Land. B 316, 143–160, 1987) and G. A. Robinson et al. (in Sensors and Actuators, Elsevier, 1992).

The methods and corresponding kits of the present invention are capable of incorporation and practice within a variety of optical measurement systems. Specifically, while the kits and materials of the present invention may be practiced in an immunoassay format, such format itself is capable of embodiment in a variety of optoelectronic detection systems. More particularly, a variety of optical immunosensor technologies are already known that may be facilitated and implemented in the practice of the present invention. Thus, for example, devices and techniques such as reflection techniques, surface plasmon resonance, fiber optic waveguide techniques and integrated optic devices, may all be adopted and specifically configured to detect and display the results of the examination of a patient's biological sample in accordance with the present method. Particular reflection techniques, such as reflectometry and ellipsometry, and the specific use of optical fibers, optical waveguides, fluorescent capillary fill devices and integrated optical biosensors, present but a few of the variant techniques and equipment that may be employed. A general review of these devices may be found in Robinson, G. A., Optical Immunosensors: An Overview, *Advances in Biosensors*, Vol. 1, pp. 229–256 (1991).

More particularly, ellipsometry relies on the direction of a polarized light beam first against a reference surface (a standard) and thereafter against the sample surface, following which a comparison of the nature and extent of the resulting reflections can be made. Particularly, the binding of analyte to receptor molecules will be measured as a chain the thickness of the surface relative to the reference surface.

In the instance of multiple internal reflection spectroscopy, for example, the ligand and its receptor may be covalently immobilized on the optical surface of a planar, fused-quartz waveguide after which a light beam may be internally reflected within the waveguide and would penetrate into a solution adjacent the waveguide, so that refractive differences would be capable of measurement as between the standard and the sample. In this particular format, a fluorescent label may be associated and measurements of fluorescence resultingly taken to determine the present extent of binding.

An additional technique utilizes the technology known as fluorescent capillary fill device. In this particular technology, two glass plates held apart by a gap of capillary dimension are utilized. Receptor molecules may be immobilized onto the base plate which also acts as an optical waveguide. Competitive or sandwich assays utilizing FITC labeling may be performed and induced fluorescence is coupled into the waveguide with signal from bound as opposed to unbound sources. Such signal is discriminated by its angular divergence upon exiting the waveguide. Surface Plasmon Resonance (SPR) devices have also been prepared which operate in response to the coupling of light incident upon a thin metal film into surface modes associated with collective electron oscillations within the metal film. Resonance condition is dependent upon the optical characteristics of the metal film, its thickness, the refractive indices of the dielectric on either side of it, and the angle of incidence of light. Receptor molecules are bound to the top side of the metal film, and the light is directed at the bottom side of the film, such as through a prism substrate. The target analyte, when binding to these receptors, will cause a shift in the resonance condition because of the change it produces in the local refractive index. Resonance is observed by a monitoring of the reflected light intensity as the angle of incidence at the light beam on the metal film surface varies. The change in resonance angle will directly correlate with the amount of analyte bound.

The techniques involving fiber optic systems include the evanescent field fluorescence. In this instance, the cladding is removed from the end of an optical fiber, thus producing a sensor element that evanescently interacts with the surrounding medium. Receptor molecules are bound to the exposed fiber surface, and direct assays may be performed utilizing the natural fluorescence of the receptor and conjugate proteins. Competitive or sandwich assays may be performed using FITC labeling to achieve greater sensitivity. In operation, a light wave is coupled into the fiber, and a portion of the evanescently produced fluorescence is coupled back into the fiber and propagated back to a detector.

A further technique utilizing optical fiber technology involves the optical fiber capillary tube, in which a bare fiber optic is enclosed within a cylindrical fill chamber, producing a sensor element that interacts evanescently with the portion of the fill volume immediately surrounding the fiber. Receptor molecules may be bound to the exposed fiber surface and sandwich or competitive displacement assays may be performed. A light wave would be coupled into the fiber, and a portion of the evanescently-induced fluorescences would be coupled back into the fiber and propagated back to a detector. The signal from the target analyte versus the background sources is discriminated by its angular divergence upon exiting the fiber. Other fiber optic techniques, such as fiber optic fluorescence may be adapted to the present invention utilizing certain of the same principles enunciated above.

Further photonic techniques such as interferometry include the disposition of a thin-film waveguide having, for example, two paths, on the first of which receptor molecules may be immobilized while the second is shielded to provide a reference channel. Laser light, for example, may be coupled into the waveguide and split down the two paths, so that changes in the refractive index and thickness of the covering letter may be detected by the result of a phase shift in the beam, that will, in turn, correlate with the amount of analyte bound. A variation on this approach is identified in the Hartman interferometer, where a single path multimode thin film planar waveguide is prepared. Receptor molecules may be immobilized on this path, and light from a laser may be coupled into the waveguide so that two modes propagate down the path. The optics of multimode geometries are such that the higher order mode has a large evanescent field, providing a signal mechanism, and the lower order mode has practically no evanescent field, providing a reference mechanism. Binding with the target analyte will cause related changes in the refractive index and thickness of the covering layer over the path which will be detected by the evanescent field of the higher order mode, causing a phase shift in that mode. As the lower order or reference mode is blind to such changes, no phase shift will be experienced, and the measured difference between the signal and reference beams will be capable of correlation to determine the amount of analyte bound.

While the foregoing discussion has provided both in general terms and some detail, various techniques available in optical sensor technology are adaptable to the practice of the present invention. It is to be understood that the above recitation is by no means exhaustive or limitative, as a variety of extant technologies may be adopted, that will successfully measure differences in binding and, consequently, the presence and amount of the respective markers or analytes of interest herein. Of course, as emphasized above, no matter what technology is employed, the practice of the invention comprises simultaneous detection and measurement of at least three analytes.

Diagnosis of Cardiac Disorders

In one example of the present invention, the first analyte is the ischemic marker myosin light chain (MLC), the second oro diagnostic analyte is myoglobin, and the third analyte is CK-MB which is a cardiac tissue specific ischemic marker.

If the results shows positive for MLC and negative for both myoglobin and CK-MB, it would indicate that the patient's chest pain is cardiac in nature, resulting from ischemic changes in the heart, and unstable angina would be the diagnosis.

If myoglobin and MLC which both appear early in the development of MI are positive and CK-MB which appears at elevated levels about 6 hours after onset of chest pain is negative, it would indicate an early evolving myocardial infarction within 6 hours of onset, and thrombolytic intervention therapy could be initiated. If all three are positive, it would indicate a myocardial infarction within 6 to 8 hours of onset of chest pain. The device of this example is not capable of alerting the physician to the exact duration of the MI, i.e., whether it has been in process for more than 6 hours. If the less than 6 hour marker were replaced with a marker which comes out after 6 hours, this information could be obtained.

If all three markers are negative, the patient is not experiencing an ischemic event.

Although the practice of the present invention with three markers is suitable for many emergency room situations, a higher degree of specificity may be attained by the use of four markers as explained above.

In an example of the present invention using four markers, two of these markers are MLC and troponin-I, both of which are ischemic markers. The other two markers are exclusively MI-specific. One of the MI specific markers is myoglobin, which is present in the blood stream at early stages of an MI (less than 6 hours), and another MI-specific marker is CK-MB, which is present at elevated levels in the blood stream after 6 hours. With this combination of markers, the physician will be able to determine if the chest pain is an ischemic event, and if it is, whether it is UA or MI. In addition, because each of the MI markers to be tested presents itself at different times in the blood stream following chest pain, the physician will also be able to tell if the duration of the MI is more or less than 6 hours.

According to this embodiment of the present invention, if the results show positive for myosin light chain and/or troponin-I, but negative for both myoglobin and CK-MB, it would indicate that the patient's chest pain is an ischemic event diagnosed as UA. If myoglobin and myosin light chain and/or troponin-I are positive and CK-MB is negative, it would indicate an early MI within 6 hours of onset and intervention therapy could be initiated successfully. If all markers are positive, it would indicate an MI of more than 6 hours duration.

Description of Preferred Embodiments

In a particular embodiment described hereinbelow, the invention is directed to an assay device which relies on a sandwich format for immunodetection of each of the markers.

In this embodiment, the detector antibody is labelled with an indicator, i.e. a colored label or an enzyme which will produce a color, that will ultimately yield a detectible reaction. Thus, the patient's blood would first require some pre-filtering in order to remove the red blood cells so that the color of the red blood cells will not interfere with the colored labels. If radioactive labels or fluorescent labels were to be used, a pre-filtration or centrifugation step may not be required.

Figure 8:
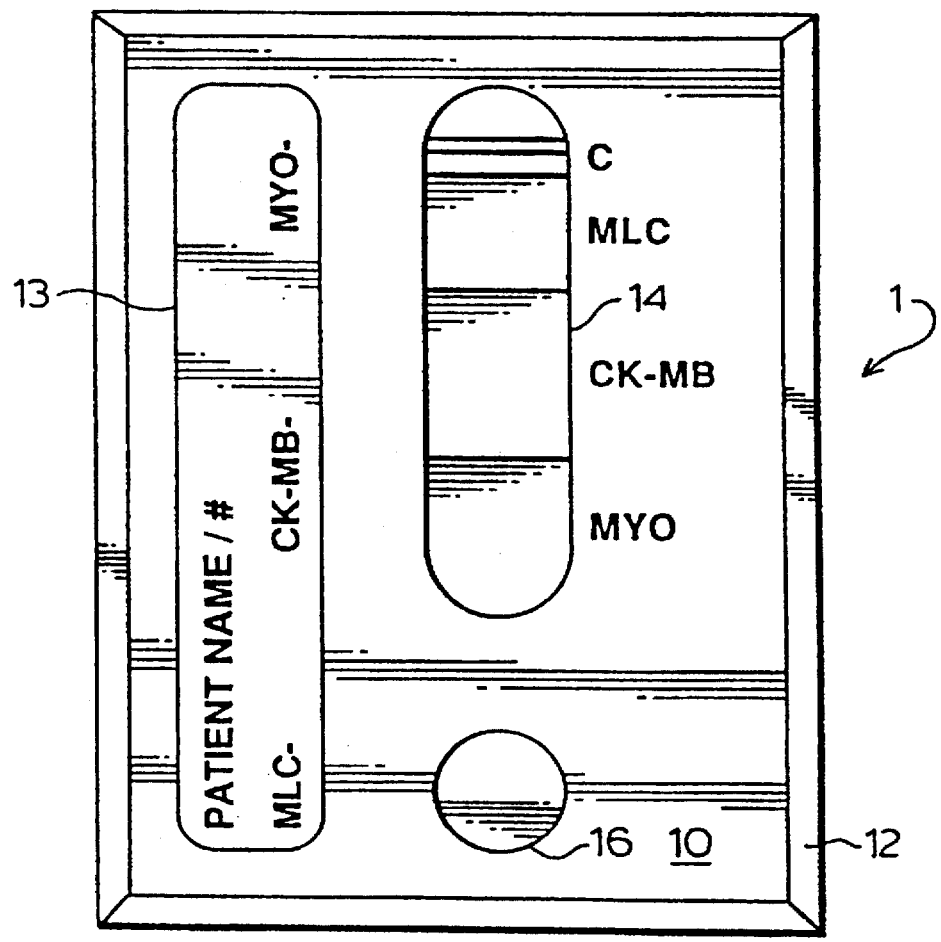
FIG. 8 is a plan view of one embodiment on the present invention.
Figure 9:
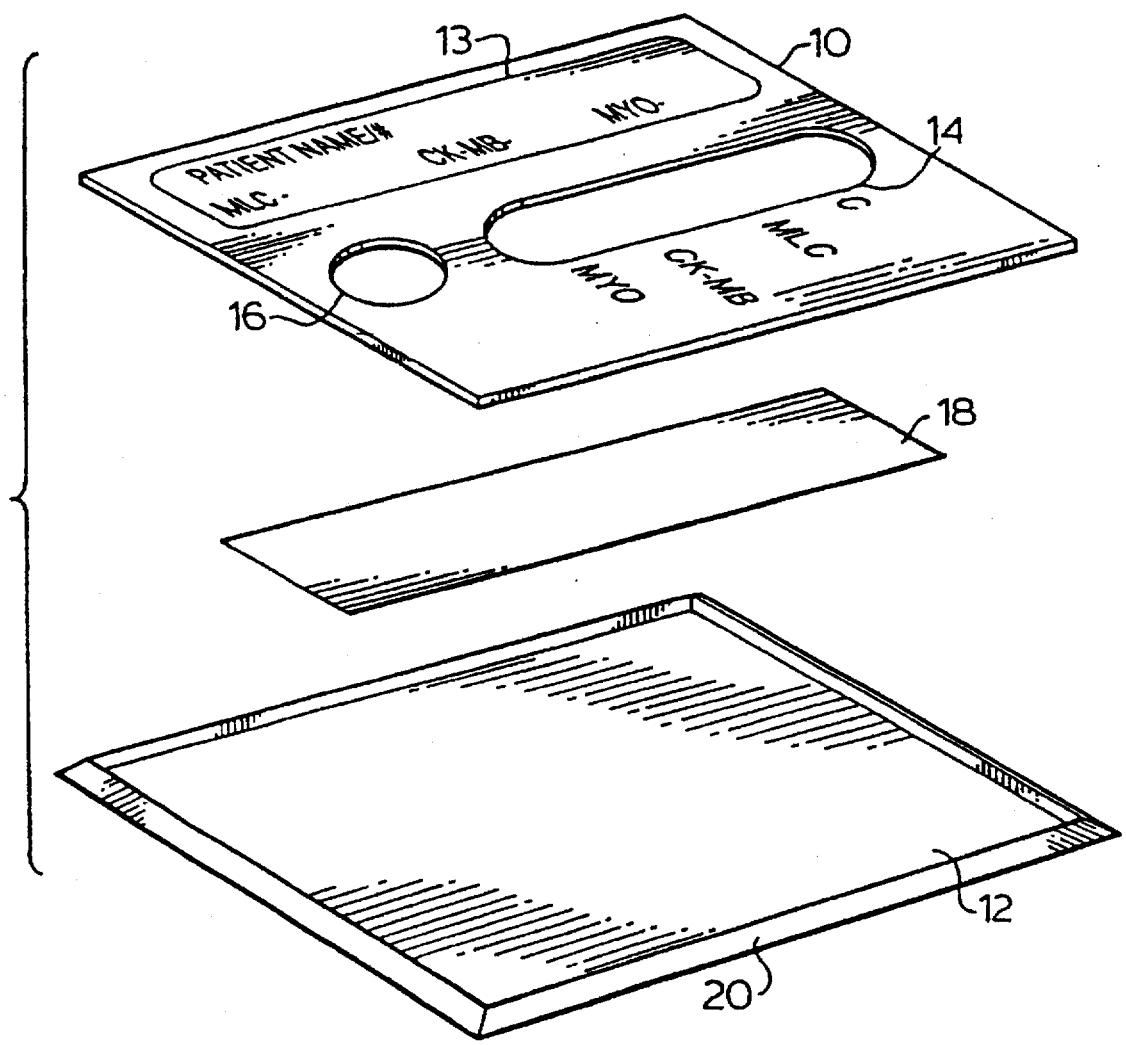
FIG. 9 is an exploded perspective view of the embodiment of FIG. 8.
Figure 12:
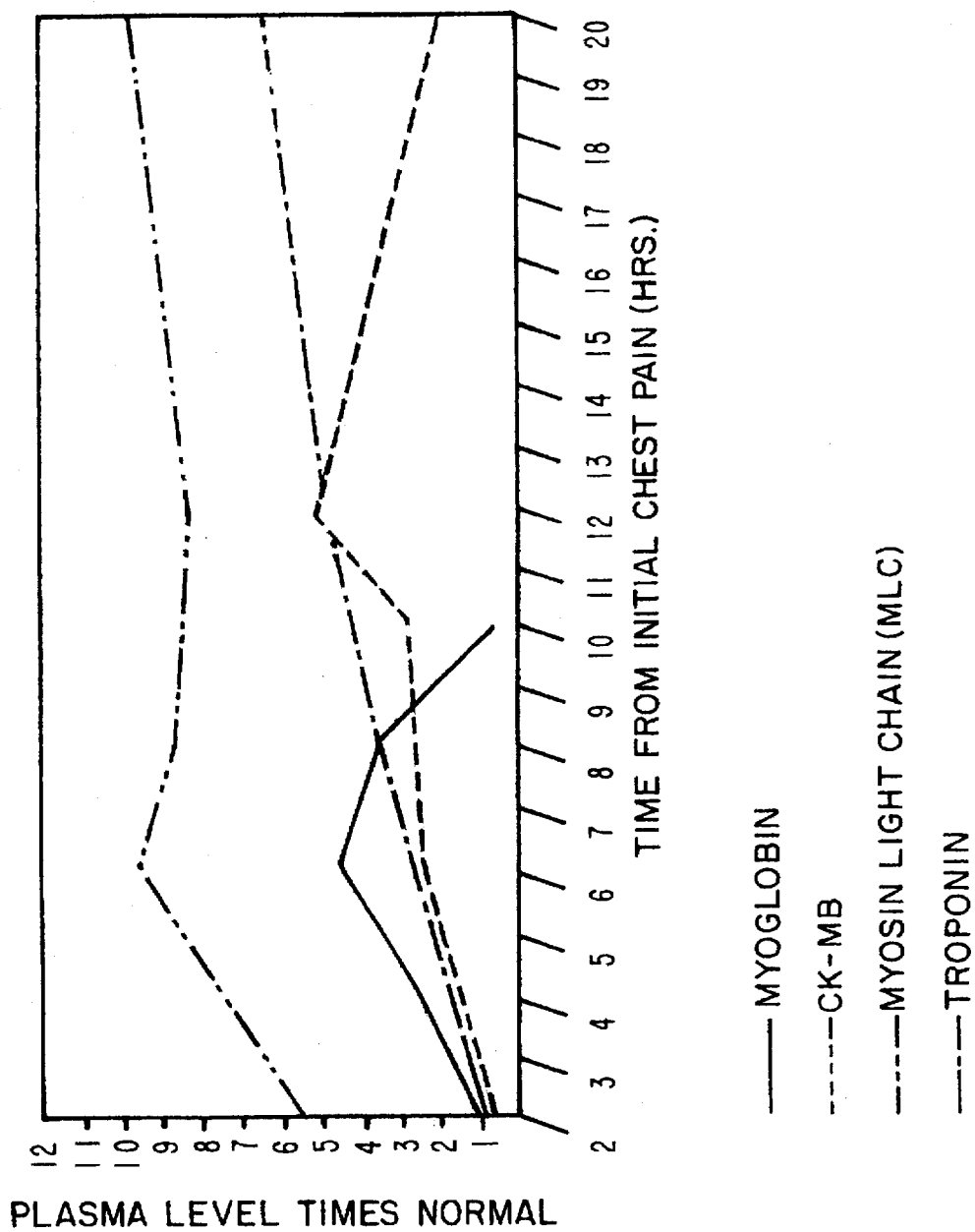
FIG. 12 is a graph illustrating the temporal variation in the concentration of four representative protein markers indicative of cardiac condition and status.

This embodiment of the invention is illustrated in FIGS. 8 and 9. A panel format is shown as indicated in general by reference numeral 1. Panel 1 consists of a polypropylene card having a front panel 10 and a back panel 12. Front panel 10 has a display window 14, to view the cardiac markers after they have reacted and show a color, and a sample window 16, as illustrated in FIG. 8. Underneath the front panel 10 is a filter membrane 18, which is affixed to the back of front panel 10 by suitable means. Back panel 12 is provided with a lip 20, which extends around the perimeter of back panel 12 for receiving front panel 10 in a snap fit thereby sealing the membrane 18 between the front and back panel.

While the front and back panels have been described as being snapped together, there are numerous other suitable methods of joining the two together which would be apparent to a person skilled in the art.

Front panel 10 may also be provided with an area 13 upon which the patient's name or identification may be written. Also space may be available to write the results of the test.

With reference to FIG. 10, membrane 18 is the carrier of the detector and capture antibodies. In this embodiment, the flow of serum or plasma is by capillary action and is in a direction from end 22 to the opposite end as indicated by the arrow. A first detector antibody 24 is layered onto the membrane 18. First detector antibody 24 is dye labelled and is specific to a first marker to be detected. Said first detector antibody is reversibly bound to the membrane. First capture antibody 26 is immobilized onto membrane 18 immediately adjacent to and downstream from first detector antibody 24. First capture antibody 26 is specific to a second epitope of said first marker to be detected.

Similarly, second detector antibody 28 is layered onto the membrane 18. Second detector antibody 28 is dye labelled and is specific to a second marker. Second capture antibody 30 is immobilized onto membrane 18 immediately adjacent to and downstream from the second detector antibody 28. Second capture antibody 30 is specific to a second epitope of the second marker.

Similarly, third detector antibody 32 is layered onto the membrane 18. Third detector antibody 32 is dye labelled and is specific to the a third marker. Third capture antibody 34 is immobilized onto membrane 18 immediately adjacent to and downstream from the third detector antibody 32. Third capture antibody 34 is specific to a second epitope of the third marker.

As discussed previously, one of said markers is MI-specific, two of said markers are ischemic markers, one of which is cardiac-specific. Such immunological specificity may be attained by screening suitable antibodies for their recognition of the particular peptide sequence of a marker, for example, the marker troponin-I. Alternately, the antibody or binding partner in question may be engineered to contain a particular region or sequence previously determined to demonstrate such immunospecificity. The region of the antibody where such immunospecificity is usually present is at the amino terminal end of the molecule, and this region can be examined to identify the particular sequence or site of interest. All of the foregoing may be performed by procedures known in the art.

In addition, a control detector antibody 36 is layered onto the membrane 18. Control detector antibody 36 is dye labelled and is specific to any protein found in normal serum or plasma. Control capture antibody 38 is immobilized onto membrane 18 immediately adjacent to and downstream from the control detector antibody 36. Control capture antibody 38 is specific to a second epitope of this control protein. The control does not necessarily require an antigen/antibody reaction. Any of a number of reactions which will be known to the skilled artisan may be employed.

According to this embodiment of the present invention, the detector antibodies are reversibly immobilized upon the solid support whereas the capture antibodies are irreversibly immobilized. Further elements, which could be included in the test panel of this embodiment, but not shown in FIGS. 9 and 10, include a reservoir pad to which the sample and, where appropriate, buffers are added. The buffers ensure proper migration of the sample through the solid support, and may be added in certain instances if the sample size is small, for example about 50 μl. The reservoir pad may also include the necessary reagents required to develop an indirect label for detecting the presence of the detector antibody-analyte-capture antibody complex, if the detector antibody is not visually labelled with a direct label.

The reservoir pad will have sufficient porosity and volume to receive and contain a liquid sample on which the assay is to be performed. The reservoir pad can be positioned at end 22 of the membrane 18. At the other end of the membrane 18, also not shown in FIGS. 9 and 10, can be positioned a wicking membrane which will facilitate the migration of the sample through the filter membrane 18.

Figure 14:
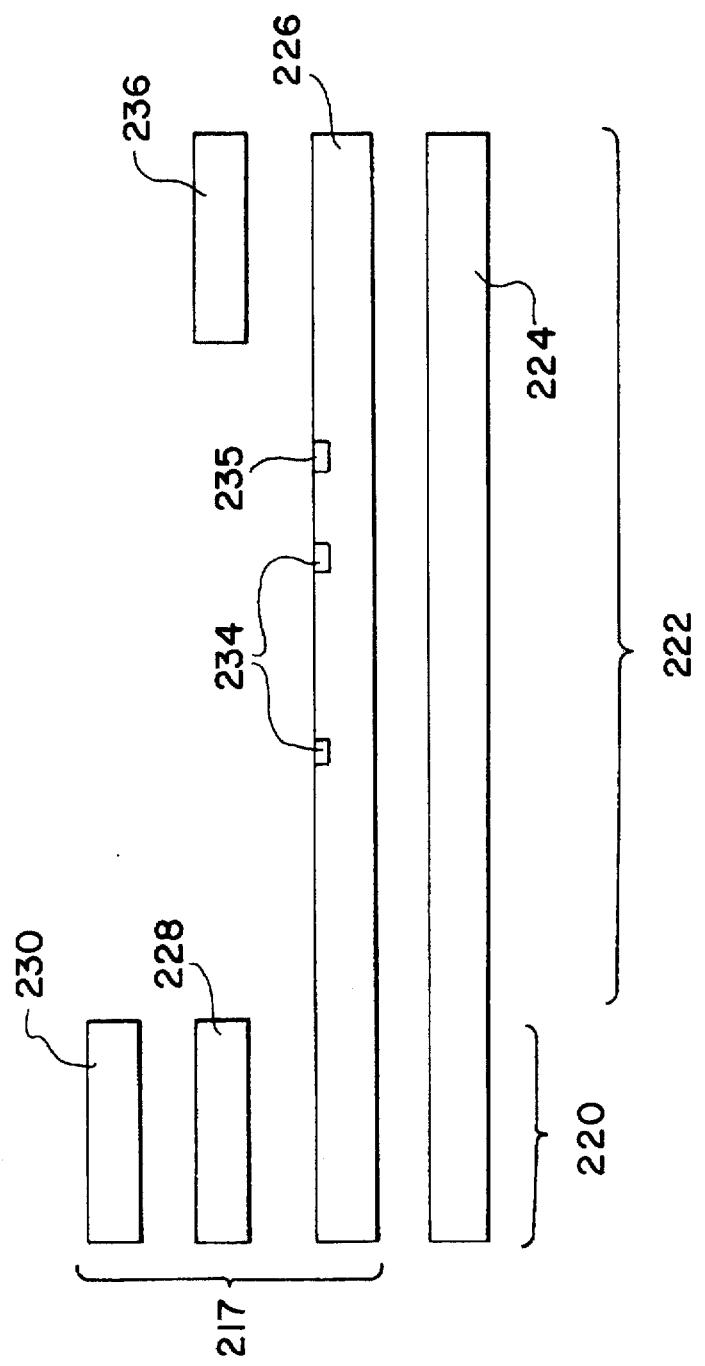
FIG. 14 is an exploded schematic view of the interior components of the device of the embodiment of FIG. 13.
Figure 15:
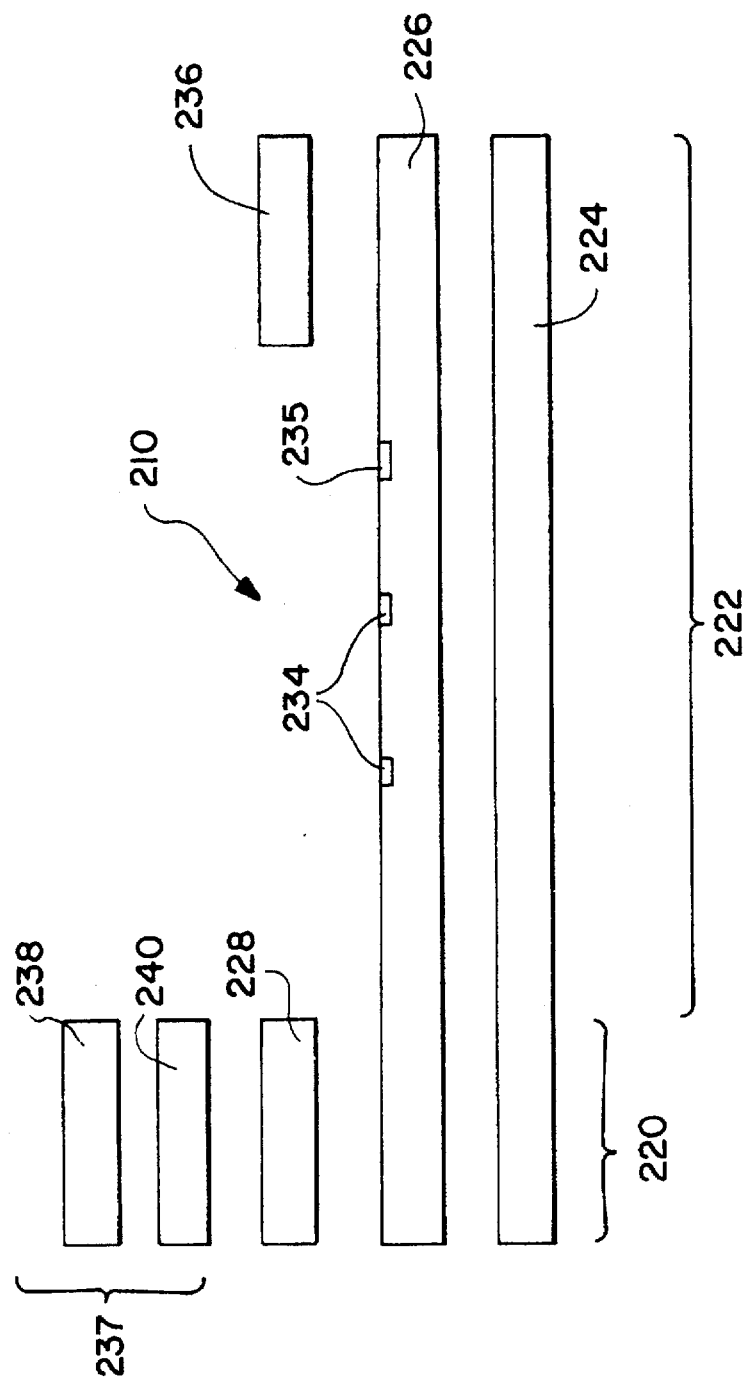
FIG. 15 is an exploded schematic view similar to FIG. 14, of a further embodiment of the present invention.
Figure 16:
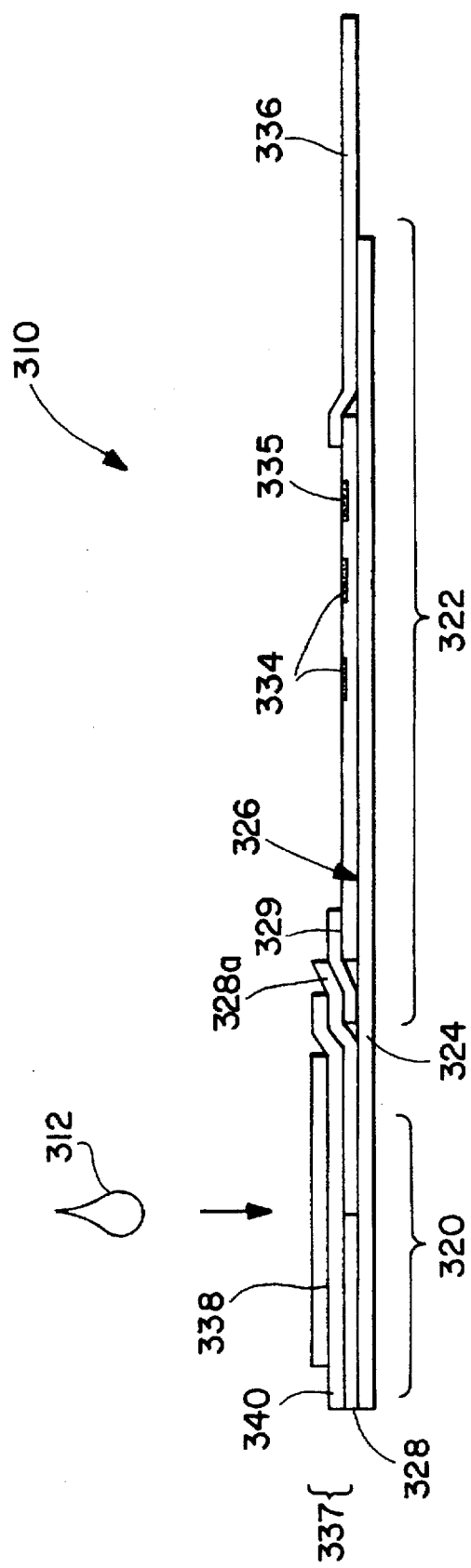
FIG. 16 is a schematic side view of a test device in accordance with an alternate embodiment of the invention.

The reservoir pad, the filter membrane and the wicking membrane are illustrated schematically in FIGS. 14–16 discussed infra, and may be fashioned from any number of filter materials. Typical materials for use in the filter membrane are hydrophilic materials which include, but are not limited to, polyurethane, polyacetate, cellulose, fiberglass and nylon with pore sizes in the range of 0.45–60 μm. Typical materials for use in the wicking membrane and reservoir pad include, but are not limited to nylon, cellulose, polysulfone, polyvinylidene difluoride, cellulose acetate, polyurethane, fiberglass, and nitrocellulose.

In use, the diagnostician, for example a physician, ambulance attendant or nurse, adds three drops, or less than 100 μl, of the patient's serum or plasma to the sample window 16. The sample will migrate along the membrane 18 by capillary action and will successively come into contact with the detector antibody and capture antibody pairs 24 and 26, 28 and 30, 32 and 34 and 36 and 38.

If the specific marker or analyte is present in the serum or plasma, the particular analyte will specifically bind with the detector antibody, which in this embodiment is dye-labelled. The detector antibody-analyte complex formed will travel by capillary action to the immobilized capture antibody. The complex will then specifically bind with the immobilized capture antibody and a color change will be experienced in a focused, distinct band at the site of the immobilized capture antibody. The color change is proportional to the concentration of the cardiac marker in the sample. Therefore if the test kit is used in timed intervals the increase or decrease in marker concentration can also be determined and used as a diagnostic tool. The results of the test should be completed within 3–5 minutes.

In a second embodiment as illustrated in FIG. 11, filter membrane 118 may have a plurality of layers on which first detector antibody 124 is layered onto a top layer of the filter membrane 118. First detector antibody 124 is dye labelled and is specific to a first marker. First capture antibody 126 is immobilized onto a middle layer of membrane 118 immediately below and downstream (the direction of flow is shown by the arrow in FIG. 11) from first detector antibody 124. First capture antibody 126 is specific to a second epitope of the first marker to be tested. Similarly for each other marker to be detected, a corresponding pair of a detector antibody with label and a capture antibody are provided, i.e., 128 and 130, 132 and 134 and control pair 136 and 138. In use, the sample of serum or plasma is added to the top layer of membrane containing the detector antibodies. As with the preceding example, a suitable buffer to facilitate the flow of the sample through the device may also be added. If the specific marker or analyte is present in the serum or plasma, the particular analyte will specifically bind with the detector antibody, which in this embodiment is dye-labelled. The detector antibody-analyte complex formed will travel by capillary action to the immobilized capture antibody. The complex will then specifically bind with the immobilized capture antibody and a color change will be experienced in a focused, distinct band at the site of the immobilized capture antibody.

The filter membrane 118 can be supported by absorbent material 120 which will function in a manner similar to that described for the wicking membrane as described above. Absorbent material 120 will enhance the draw of the sample through the membrane.

In the preceding examples, each of the detector antibodies for each of the cardiac analytes is in a separate detector section in close proximity to a separate capture section containing the corresponding capture antibody. These types of panels are difficult to prepare and thus a further panel was developed wherein all of the detector antibodies are located in a single detector section and will migrate with the sample, when in use, to the capture section. The capture antibodies, in this example of the device, are irreversibly immobilized at discrete positions within the capture section, basically as described above for the other panels.

Figure 13:
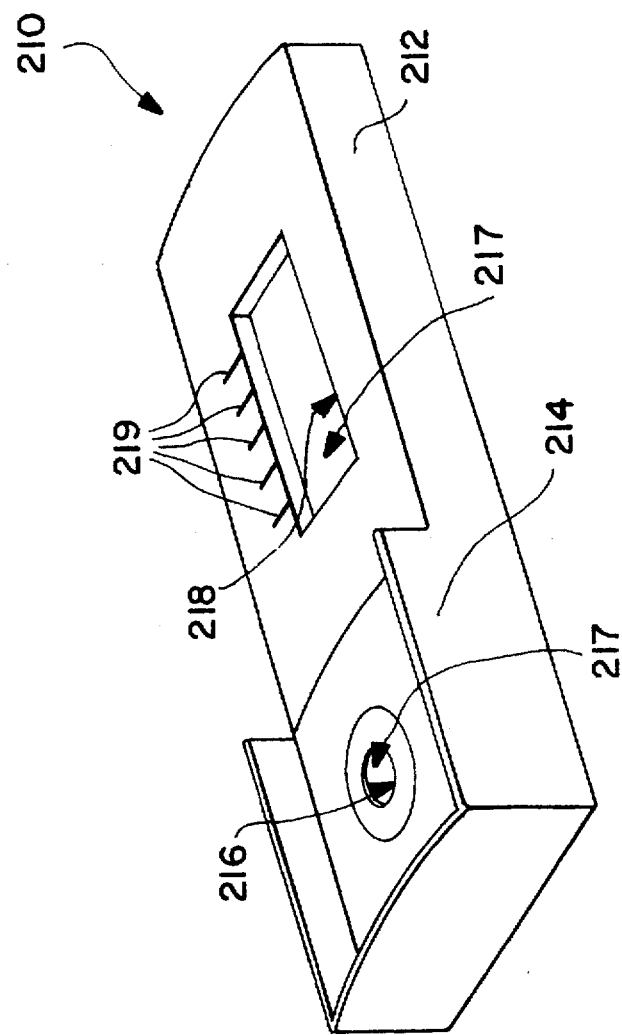
FIG. 13 is a top perspective view of a third embodiment of the present invention.

One example of this type of assay device is shown in FIGS. 13 and 14. FIG. 13 shows a schematic side view of the device of this embodiment of the invention, which is identified generally by reference numeral 210. The assay device is formed from two main components, a housing means 212 and a sample means 214.

The sampling means 214, comprises a sample opening 216, which is in fluid communication with a membrane assembly, referred to generally in FIG. 13 by reference numeral 217, which is located within the housing means and generally beneath the sample opening 216 and the display opening 218. For ease in determining the results of the test, labelled notations, referred to generally by reference numeral 219, on the side of the housing means 212, corresponding to and identifying the markers to be tested, are provided.

An exploded view of one example of the assay device is shown in FIG. 14. In this embodiment of the invention, the device and more specifically, membrane assembly 217 are seen to define two general sections, a detector section 220 located proximal to the sample opening 216, and a capture section 222 disposed downstream and distal thereto. The bottom side of the membrane assembly 217 as illustrated may be affixed to a base 224, which can be formed of any rigid material. The membrane assembly 217 is composed of a plurality of membranes and pads. The bottom layer of membrane assembly 217 is a filter membrane 226. The membrane assembly 217 further comprises a support pad 228 which is interposed between the filter membrane 226 and an absorbent pad 230, which is optional. The support pad 228 is positioned such that it is in fluid communication with the filter membrane 226.

The support pad 228 contains the detector antibodies or reagents corresponding to each of the markers to be tested in the sample. The detector antibodies are preferably labelled, as has previously been discussed. Although a direct label is preferred, an enzyme label may be used, in which case all of the reagents required for reaction and development of the colored signal would also be contained within the reagent pad 228. The support-pad can be composed of a number of pads.

It has been found that certain reagents do not work well when mixed with other reagents. For example, it has been found that the myoglobin detector antibody should be in a support pad without any other detector antibodies. A membrane assembly illustrating the use of plural pads is shown in FIG. 16 and described later on herein.

The capture section 222 of the composite membrane comprises capture antibodies, referred to generally in FIG. 14 by reference numeral 234, corresponding to each of the markers to be tested and positioned at discrete locations irreversibly immobilized to the filter membrane 226. The location of the capture antibodies corresponds with the display opening 218 and the labelled notations 219 on the side of the housing means 212. The capture antibodies are immobilized onto the filter membrane by well established procedures known in the art.

Distal to the position of the capture antibodies is a wick member 236 which is disposed on the filter membrane 226. This wick member will enhance the draw of the sample and reagents through the filter membrane.

The wick member, the absorbent pad, the support pad and the filter membrane are fashioned from any number of filter membranes. Typical materials for use in the filter membrane 226 are hydrophilic materials which include, but are not limited to, polyurethane, polyacetate, cellulose, fiberglass, and nylon with pore size of 0.45-60 µm. Typical materials for use in the wicking member and absorbent pad includes, but is not limited to, nylon, cellulose, polysulfone, polyvinylidene difluoride, cellulose acetate, polyurethane, fiberglass and nitrocellulose. The entire array of pads, wicks and membranes is attached to a solid material, the base 224, which provides support and unity for the device. This support can be constructed from a thin sheet of glass or plastic which has been cut to a size appropriate to include the entire assay contents while providing convenience to the assay user.

In use, a sample of a patient's blood, wherein the red blood cells may have been removed, is added through the sample opening 216 to the absorbent pad, if used, or directly onto the support pad. After adding the sample a volume of carrier fluid can be added to the first wick member 230 through the sample opening 216. The liquid carrier can be any buffer solution which includes but is not limited to phosphate buffer solutions, saline, Tris-HCl, and water. The sample migrates through the reagent pad 228. In the reagent pad, if the target analytes are present in the sample, they will bind to the labelled detector antibodies. The sample continues its flow through the filter membrane 226 and on into the wick member 236. Labelled detector antibody-analyte complex, if present, then binds to the corresponding capture antibody in the capture sections 234. The presence of the analyte which has been labelled with the labelled detector antibody is clearly visible through the display opening 218, at the position of the corresponding capture antibody. A control analyte, control detector antibody and control capture antibody will be also be provided in the device.

Referring now to FIG. 15, a variant embodiment of device 210 is shown that includes a filtration section, generally referred to by reference numeral 237, which would remove the red blood cells from the sample and thus eliminate the need for pre-centrifugation or pre-filtration of the sample. This device would be most suitable for use by a paramedic or other individuals outside of the confines of a hospital, where centrifugation or filtration devices would not be readily available. The filtration section comprises a filtration member 238 attached directly to the sample means 214 (in a manner not illustrated, however), wherein the filtration member 238 is disposed on the underside of the sample means 214 and covers the sample opening 216. There are a number of filter membranes which can be used according to this example of the present invention. These have been disclosed in Canadian Patent 949,865 and Canadian Patent 1,177,374, and U.S. Pat. No. 5,240,862.

According to the device disclosed in U.S. Pat. No. 5,240,862, the filter membrane is a separator membrane, which preferably is an asymmetric membrane. When in use the blood fluid together with the particulate material, if any is present, penetrates immediately into the pores, wherein the particulate materials are retained in the pores, which are becoming gradually smaller, whereas the clear part (e.g., plasma component) of the body fluid penetrates further. An additional feature of U.S. Pat. No. 5,240,862, which is particularly useful according to the present invention, is a collector membrane 240, which is in separable contact with the filtration member or separator membrane 238, positioned between the separator membrane and the reagent pad of the detector section. Collector membrane 240 is a hydrophilic membrane with a defined pore volume, and will thus retain a known volume of sample. Therefore, a particular analyte in the sample can be determined quantitatively. For further details concerning the membranes and their configuration, refer to U.S. Pat. No. 5,240,862.

In use, approximately 150 µl of blood is added to the separator membrane 238 through the sample opening 216. The separator membrane will retain the particulate material in the blood and allow the plasma to filter through the membrane into the collector membrane. The pore volume of the collector membrane is chosen to allow the retention of 50 µl of plasma. The sample means, with attached separator membrane is then removed from the device. A liquid carrier, as described above, is then added to wash through the sample from the collector membrane into the detector section, which contains the reagent pad(s) containing the detector antibodies. If the target analytes are present in the sample, they will bind to the labelled detector antibodies. The sample continues its flow through and across the filter membrane 226 and on into the wick member 236. Labelled detector antibody-analyte complex, if present, then binds to the corresponding capture antibody in the capture section. The presence of the analyte which has been labelled with the labelled detector antibody is clearly visible through the display opening 218, at the position of the corresponding capture antibody. A control analyte, control detector antibody and control capture antibody will be also be provided in the device.

A further variant construction is shown in FIG. 16, where device 310 can be seen to resemble device 210, with the inclusion of a filtration section 337 that includes a filtration member 338 that may be fabricated from a membrane having an asymmetric pore distribution, to effectively retain unwanted particulate material present in the blood sample, depicted schematically at 312. Filtration section 337 further includes a collector membrane 340 that receives the sample passing through filtration member 338. The sample then flows into support pad 328 which functions in similar fashion to support pad 228 in the disposition of one or more antibody detectors having the desired immunospecificity. In the embodiment illustrated in FIG. 16, multiple reagent pads are shown and particularly, pads 328a and 329 are depicted, that contain particular reagents that have been desirably segregated from each other to prevent their cross-reaction during initial recognition of analytes in the sample as it travels toward capture membrane 326.

The sample thus passes from pads 328, 328a and 329 and flows along capture membrane 326, where it will encounter capture antibodies 334 and control 335. Spent sample will thereafter be received by wick member 336.

As mentioned previously, the detector and capture antibodies of the present invention can be prepared by standard techniques well known in the art. However, when monoclonal antibodies are used in the flow-through devices as described above, antibodies with a high immunospecificity for the marker are required. This requirement results from the dynamics of the flow through system. The antibodies are only in contact with the analytes for a brief period of time and thus the antibodies, used in these embodiments of the present invention, must be high affinity antibodies and must be highly immunospecific for the particular analyte against which they were raised.

The antibodies proposed for use as detector antibodies are first screened against the analyte to choose a high affinity antibody. Antibodies with a binding constant ranging from $10^8$ to $10^{11}$, as determined using the BIAcore™ system (Pharmacia Biosensor AB, Uppsala, Sweden), are preferred. The detector antibodies may preferably also be affinity purified against other human serum proteins such as human serum albumin and human IgG, to ensure that the antibody will not cross-react with these proteins. Many of the cardiac proteins share homology with each other and, therefore, a detector antibody specific for one cardiac analyte may have some cross-reactivity with other cardiac proteins. This problem can be overcome by affinity purifying out any detector antibody which shows cross-reactivity with other cardiac analytes. Alternatively, in the cardiac panel where the detector antibody and capture antibody are present in close alignment on the filter membrane, a monoclonal antibody which exhibits cross-reactivity with other cardiac analytes can be placed at the end of the panel so that this monoclonal antibody will not have an opportunity to cross-react with other analytes. In the example where all of the detector antibodies are present together in a reagent pad, the detector antibodies must, in this case, be specific for the analyte it was raised against and antibodies which exhibit cross-reactivity with other cardiac analytes should be screened out.

The antibodies sometimes will cross-react with each other and, therefore, in the example where all detector antibodies are present in the reagent pad, it may be necessary to adjust the pH of the reagent pad to ensure that the antibodies do not bind to each other. The range of pH of the reagent pad is generally from 6–8.

Some of the cardiac markers assayed for in the present invention appear in the blood in non-cardiac conditions. In other words, normal patients will have a basal level of some of the cardiac markers in their blood at all times. Accordingly, in the present invention, the diagnostic test and device must determine when the markers are above their basal level. This could be accomplished in a number of ways. For example, the concentration of the levels of cardiac markers in the blood can be determined and compared to the levels in a normal population.

Although according to the present invention, any increase over the basal level could be considered as a positive result, in order to improve the sensitivity of the test and to take into consideration individual variation of basal levels, the diagnostic device of the present invention is preferably configured such that a positive result will only be indicated when the selected markers being analyzed are 2 times higher than the basal level. Thus, in a specific embodiment, the "threshold level", as defined earlier herein and according to the present invention, is defined as 2X the basal level for a particular analyte.

The basal level of the different markers in normal volunteer blood donors can be determined empirically. For example, it has been found that the basal level of the following cardiac markers, used in one of the embodiments of the present invention, is as follows: myoglobin light chain, 1 ng/ml; troponin-I, 0.8 ng/ml; myoglobin, 100 ng/ml; and CK-MB, 5 ng/ml.

There are a number of methods which can be used to ensure that concentrations of analyte, below the threshold level, do not exhibit a positive result. Varying the ratio of detector antibodies to capture antibodies will determine the sensitivity or the level of detection. One can also vary the sensitivity of the antibodies, providing either a low or high affinity antibody. For example, in the flow-through type immunoassay device of the present invention, the flow is very fast. Thus, if one were to use a low affinity antibody as a detector antibody for the analyte, small concentrations of the analyte will pass undetected. In a further example, the detector antibodies is a mixture of labelled and unlabelled antibodies. The ratio of the concentration of the labelled detector antibody to the unlabelled detector antibody will depend upon the analyte to be tested and its threshold level. The concentration is varied such that the analyte, below the threshold level, will bind preferentially to the unlabelled detector antibody, but once the concentration of the analyte is above the threshold level, then the analyte will bind preferentially to the labelled detector antibody. For example, one could use high affinity unlabelled antibodies to absorb analyte up to the threshold level and low affinity labelled antibodies to absorb analyte in excess of the threshold level.

The binding capacity of the capture antibody for the analyte is lower than the binding capacity of the analyte for the detector antibody. Otherwise, the capture antibody would bind the analyte and the labelled detector antibody may be lost. Therefore a potentially positive result would go undetected. The range of the binding capacity for the antibodies, either capture antibody or detector antibody, is from $10^8$–$10^{11}$, as detected using the BIAcore™ system. These antibodies are all considered high affinity, and when the present specification refers to a low affinity antibody, then it is meant that it is the lower range of these high affinity antibodies.

The concentration of the antibodies in the test panel ranges from 2–5 mg of capture antibody and 0.5–1 mg of detector antibody, or the labelled part of the detector antibody.

The panel of the present invention can be used to distinguish the non-cardiac chest pain from cardiac chest pain and to distinguish unstable angina from a myocardial infarction as set forth the in the following examples, which are not to be construed as limiting.

EXAMPLE 1

Biochemical Triage of Chest Pain Patients in Emergency Department Using a Panel of Specific Cardiac Markers Patients admitted to the CCU (cardiac care unit) of a local hospital were included in this study. Five different groups of patients were studied as follows:

1. Patients with Acute Ischaemic Coronary Artery Syndromes (Myocardial Infarction, Unstable Angina, Stable Angina).
2. Patients with cardiac non-coronary conditions (presenting with chest pain). This population includes patients with CHF, Syncope, Arrhythmias, Pericardial Diseases.
3. Patients with non-cardiac conditions (Presenting with chest pain).
4. Surgical patients with cardiac risk factors (To merit Post-Operative monitoring for cardiac complications). This population includes
   a) Patients who developed acute cardiac ischaemic conditions (MI, UA, CHF);
   b) Patients who did not develop cardiac complications.
5. Hospitalized non-cardiac patients presenting to the Emergency Department.

The blood samples were collected and stored at −70° C. and analyzed in batches. The level of various markers [Myosin Light Chain 1 (MLC1), Troponin I (Tn I), Myoglobin and CK-MB isoenzyme] was measured by using an immunoassay format of the present invention, as depicted in FIGS. 13 and 14. The clinical data was collected and the analysis was done retrospectively.

The level of different markers in normal volunteer blood donors was determined and the results were as follows (for all of the markers n=171):

The 98 percentile of various markers was as follows in Table 5:

TABLE 5

| Marker | Value |
|---|---|
| MLC1 | 1 ng/ml |
| TnI | 0.8 ng/ml |
| Myoglobin | 100 ng/ml |
| CK-MB | 5 ng/ml |

The different coronary syndromes could be differentiated on a biochemical basis depending on the elevated marker above the normal values in the first blood sample collected in the emergency department as shown in Table 6:

TABLE 6

| | Stable Angina (SA) (n = 48) | Unstable Angina (UA) (n = 80) | Myocardial Infarction (MI) (n = 109) |
|---|---|---|---|
| Age: | | | |
| Mean: | 61 | 59 | 67 |
| Range: | 43–89 years | 37–78 years | 41–94 years |
| male/female ratio | 2:1 | 3:1 | 2:1 |
| Myoglobin | 2% | 0% | 66% |
| CK-MB | 0% | 0% | 59% |
| MLC1 | 10% | 72% | 88% |
| TnI | 2% | 35% | 41% |

Acute cardiac non-coronary conditions (CHF, Syncope, Arrhythmias, Pericardial diseases) presenting with chest pain (n=54) are shown as follows in Table 7:

TABLE 7

| Age: | |
|---|---|
| Mean | 69 years |
| Range | 42–85 |
| Male/Female Ratio: | 1:1 |
| Myoglobin | 33% |
| CK-MB | 6% |
| MLC1 | 59% |
| TnI | 12% |

In this population, more than two markers were elevated in only 9% of the patients. Therefore, the specificity for biochemical identification of cardiac patients experiencing cardiac events is 91%.

Results from patients with non-cardiac conditions (pulmonary embolism, dyspnea, indigestion, musculoskeletal pain, pneumothorax) presenting with chest pain (n=25) are shown as follows in Table 8:

TABLE 8

| Myoglobin | 0% |
|---|---|
| CK-MB | 12% |
| MLC1 | 13% |
| TnI | 11% |

In this population of non-ischaemic, non-cardiac conditions, more than two markers were elevated in only 4% of the patients. Therefore, the specificity for the biochemical identification of cardiac patients with MI or UA was 96%.

According to the hospital diagnosis of surgical patients (n=42), the cardiac ischaemic conditions were detected by a combination of the four cardiac markers in 84% of cases (n=31). In contrast, in patients with no cardiac complications (n=11), two or more markers were elevated in only 1% of this group, resulting in a specificity of 99% for the biochemical identification of patients experiencing ischemic events.

In hospitalized non-cardiac patients (n=128), presenting to the emergency department, only 2 patients were positive for 2 or more markers. Therefore, the specificity for the biochemical identification of cardiac patients experiencing cardiac events was 98.5%.

The studied population is the most frequently encountered population involved in the differential diagnosis of acute ischemic coronary syndromes. By simultaneous usage of four cardiac markers, the accuracy of differentiating the various coronary ischaemic syndromes has very much increased. Particularly, this increase in accuracy is believed to be due to the temporal versatility that is achieved by the measurement of markers that are predetermined to appear strongly at different times following the onset of chest pain.

In Unstable Angina, either MLC and/or TnI is elevated in 85% of the cases. On the other hand, all of the MI patients are biochemically identified in the ED (first blood sample) by using a combination of MLC and/or TnI together with either Myoglobin or CK-MB isoenzyme.

TABLE 9

| AICS | Sensitivity | Specificity |
| --- | --- | --- |
| MI | 100% | 95% |
| UA | 85% | 87% |

EXAMPLE 2

Additional Patient Profiles

The following are representative profiles derived from patient data developed independent of the present invention, and are presented for purposes of illustrating the manner in which such data would be effectively obtained and analyzed in a clinical setting by resort to the present invention.

1. A female patient approximately 46 years of age, was examined at a cardiac care unit and indicated that chest pain had begun about 2 hours previous and had lasted for about one hour. She stated that no pain was being experienced on arrival. An EKG was performed and was normal. A blood sample was drawn and placed in the device of the present invention described with reference to FIGS. 14 and 15. Within about one half hour, the sample had been fully deposited in the device and the results were available and were reviewed by the attending physician. The strip had defined separate regions where antibodies to myosin light chain, myoglobin, CK-MB and troponin-I were deposited. The results revealed a visible color reaction in the regions containing the antibodies to MLC and myosin, however, no reaction was noted as to the region containing the antibodies to CK-MB and troponin-I.

The patient was observed for 3 hours in the emergency department, at which time a secondary test in accordance with the present invention was performed, that measured myoglobin, myosin light chain, troponin I and CK-MB. This test revealed positive readings for all factors except CK-MB and a further EKG showed evidence of an evolving anterior MI. The patient was tested for tolerance of streptokinase, and upon successful completion (a negative result), the patient was treated with streptokinase and an MI was averted.

2. A male patient 49 years old, arrived at a hospital emergency room with severe chest pain. The patient was a non-smoker with an active lifestyle. An EKG was performed and revealed non-specific changes. The test of the present invention was performed, wherein myoglobin, myosin light chain, troponin-I and CK-MB were examined and the results found to be negative. The patient was admitted and observed for a period of 12 hours in the MI rule-out unit, during which two further tests in accordance with the present invention were performed.

The test results remained negative, and the diagnosis that was reached in this instance ruled out an MI, and prompted the attending physician to discharge the patient for further outpatient observation.

3. Another patient was examined within the same time frame and who presented the same symptomatology was also tested, and in this instance, elevated levels of all four analytes were observed. The attending physician reached the diagnosis of a developing MI. Following confirmatory review of the patient's history, thrombolytic therapy was prescribed and promptly initiated. A myocardial infarct was thereby averted.

EXAMPLE 3

Representative Cost Comparisons

Two of the patient profiles presented in Example 2 above were analyzed and compared from a cost standpoint with identical profiles in which conventional diagnostic and therapeutic measures were taken. More particularly, the costs that would be incurred were patient histories 1 and 2 above carried forward with conventional therapy are compared with the costs that result when the method and test kit of the present invention is used.

In the instance of the patient in history 1, conventional diagnosis based on EKG and total CK resulted in a diagnosis that the pain was non-cardiac and the patient was sent home. Only after the pain recurred and repeated testing at the emergency department revealed a developing MI was thrombolytic therapy initiated. The differential in cost represented by the failure to earlier diagnose the condition was such as to increase by close to 50% the total costs for this episode, i.e $8,120.00 for the conventional treatment compared with $5,665.00 plus the cost of 2 test kits of the type prepared by the present invention and one anti-streptokinase test kit.

In the instance of the patient in history 2, conventional diagnosis commended the admission of the patient to the CCU and observation for three days before discharge. The cost for this patient under conventional protocols was $6,035.00 compared with $785.00 plus the cost of 3 test kits of the type prepared by the present invention. The substantial savings made possible by the present invention are clearly apparent.

All references cited herein are specifically incorporated by reference.

Although the disclosure describes and illustrates preferred embodiments of the invention, it is to be understood that the invention is not limited to these particular embodiments. Many variations and modifications will now occur to those skilled in the art. For a definition of the invention, reference is to be made to the appended claims.

What is claimed is:

1. A method for rapidly diagnosing the cause of chest pain of a patient in the early onset thereof, which method comprises the steps of:
   a) contacting a sample of scrum, plasma, or blood from a patient with at least three antibody pairs, each of which antibody pairs comprises an antibody reagent member and an immobilized capture antibody member, wherein the antibody reagent member of each antibody pair is labeled with an observable or measurable moiety, and wherein
      i) the first antibody pair specifically binds myoglobin,
      ii) the second antibody pair specifically binds CK-MB,
      iii) the third antibody pair specifically binds to a protein selected from the group consisting of myosin light chain, troponin I, and troponin T;
   whereby upon adding sample to the antibody pairs, analytes present in the sample and complementary to the antibody pairs will bind to the antibody pair; and b) visualizing or measuring the moiety and diagnosing the cause of chest pain thereby.

2. The method of claim 1 wherein the third antibody pair is specific for troponin I.

3. The method of claim 1 wherein at least one of the antibodies is a monoclonal antibody.

4. The method of claim 1 wherein at least one of the antibodies is a monoclonal antibody.

5. The method of claim 1 wherein the immobilized antibodies are located at discrete locations along a dry chemistry membrane.

6. The method of claim 5, wherein the dry chemistry membrane is affixed between a front and a back panel, wherein a) the front panel comprises a sample window and a display window, the sample window to receive a sample of serum, plasma, or blood from the patient;

b) the dry chemistry membrane is positioned for display in at least the display window; and c) the dry chemistry membrane comprises a sample region and a control region, the sample region positioned to receive the sample from the sample window.

7. The method of claim 1 which is in a dry chemistry format.

8. A diagnostic test kit for rapidly diagnosing the cause of chest pain of a patient in the early onset thereof, which kit comprises at least three antibody pairs, each of which antibody pairs comprises an antibody reagent member and an immobilized capture antibody member, wherein the antibody reagent member of each antibody pair is labelled with a measurable or observable moiety and, wherein a. the first antibody pair specifically binds myoglobin, b. the second antibody pair specifically binds CK-MB, c. the third antibody pair specifically binds to a protein selected from the group consisting of myosin light chain, troponin I, and troponin T.

9. The diagnostic test kit of claim 8 wherein the third antibody pair is specific for troponin I.

10. The diagnostic test kit of claim 8 wherein at least one of the antibodies is a polyclonal antibody.

11. The diagnostic test kit of claim 8 wherein at least one of the antibodies is a monoclonal antibody.

12. The diagnostic test kit of claim 8 wherein the immobilized antibodies are located at discrete locations along a dry chemistry membrane.

13. The diagnostic test kit of claim 12, wherein the dry chemistry membrane is affixed between a front and a back panel, wherein a) the front panel comprises a sample window and a display window, the sample window to receive a sample of serum, plasma, or blood from the patient;

b) the dry chemistry membrane is positioned for display in at least the display window; and c) the dry chemistry membrane comprises a sample region and a control region, the sample region positioned to receive the sample from the sample window.

* * * * *